(12) United States Patent
Foody

(10) Patent No.: US 10,894,969 B2
(45) Date of Patent: Jan. 19, 2021

(54) PROCESS FOR PRODUCING FUEL USING TWO FERMENTATIONS

(71) Applicant: Iogen Corporation, Ottawa (CA)

(72) Inventor: Patrick J. Foody, Ottawa (CA)

(73) Assignee: Iogen Corporation, Ottawa (CA)

( * ) Notice: Subject to any disclaimer, the term of this patent is extended or adjusted under 35 U.S.C. 154(b) by 45 days.

(21) Appl. No.: 16/244,767

(22) Filed: Jan. 10, 2019

(65) Prior Publication Data

US 2019/0144896 A1 May 16, 2019

Related U.S. Application Data

(63) Continuation of application No. 15/327,348, filed as application No. PCT/CA2015/050687 on Jul. 22, (Continued)

(51) Int. Cl.
  *C12P 7/14* (2006.01)
  *C10L 1/02* (2006.01)
  (Continued)

(52) U.S. Cl.
  CPC .............. *C12P 7/14* (2013.01); *C01B 3/38* (2013.01); *C01B 3/48* (2013.01); *C01B 3/50* (2013.01);
  (Continued)

(58) Field of Classification Search
  CPC .... C10L 3/08; C10L 1/023; C10L 3/00; C10L 1/06; C10L 1/02; C10L 1/04;
  (Continued)

(56) References Cited

U.S. PATENT DOCUMENTS 2,440,925 A * 5/1948 Boeckeler .............. B01D 3/001
  426/13
2,485,044 A   10/1949 Gehrke
  (Continued)

FOREIGN PATENT DOCUMENTS

CA   2890902 A1   5/2014
EP   450430 B1   6/1997
  (Continued)

OTHER PUBLICATIONS

Jin et al. A novel integrated biological process for cellulosic ethanol production featuring high ethanol productivity, enzyme recycling and yeast cells reuse. Energy Environ. Sci., 2012, 5, 7168. (Year: 2012).*

(Continued)

*Primary Examiner* — Sean C. Barron
(74) *Attorney, Agent, or Firm* — Knobbe, Martens, Olson & Bear, LLP

(57) ABSTRACT

A process is provided for forming a fuel or a fuel intermediate from two fermentations that includes feeding an aqueous solution comprising a fermentation product from a first bioreactor to a second bioreactor and/or a stage upstream of the second bioreactor, which also produces the fermentation product. The aqueous solution may be added at any stage of the second fermentation and/or processing steps upstream from the second bioreactor that would otherwise require the addition of water. Accordingly, the product yield is increased while fresh/treated water usage is decreased.

19 Claims, 4 Drawing Sheets

Related U.S. Application Data 2015, now Pat. No. 10,202,622, which is a continuation-in-part of application No. 14/563,116, filed on Dec. 8, 2014, now Pat. No. 9,108,894.

(60) Provisional application No. 62/115,273, filed on Feb. 12, 2015, provisional application No. 62/027,370, filed on Jul. 22, 2014.

(51) Int. Cl.

| | | |
|---|---|---|
| *C10L 3/08* | (2006.01) | |
| *C01B 3/48* | (2006.01) | |
| *C01B 3/38* | (2006.01) | |
| *C12P 7/10* | (2006.01) | |
| *C10G 2/00* | (2006.01) | |
| *C01B 32/50* | (2017.01) | |
| *C07C 29/151* | (2006.01) | |
| *C12P 7/06* | (2006.01) | |
| *C10L 3/00* | (2006.01) | |
| *C12F 3/10* | (2006.01) | |
| *C12P 5/02* | (2006.01) | |
| *C12P 7/54* | (2006.01) | |
| *C10L 1/06* | (2006.01) | |
| *C01B 3/50* | (2006.01) | |
| *C10L 1/04* | (2006.01) | |

(52) U.S. Cl.
CPC .......... *C01B 32/50* (2017.08); *C07C 29/1518* (2013.01); *C10G 2/50* (2013.01); *C10L 1/02* (2013.01); *C10L 1/023* (2013.01); *C10L 1/04* (2013.01); *C10L 1/06* (2013.01); *C10L 3/00* (2013.01); *C10L 3/08* (2013.01); *C12F 3/10* (2013.01); *C12P 5/023* (2013.01); *C12P 7/06* (2013.01); *C12P 7/065* (2013.01); *C12P 7/10* (2013.01); *C12P 7/54* (2013.01); *C01B 2203/025* (2013.01); *C01B 2203/0233* (2013.01); *C01B 2203/0244* (2013.01); *C01B 2203/0283* (2013.01); *C01B 2203/043* (2013.01); *C01B 2203/0405* (2013.01); *C01B 2203/0475* (2013.01); *C01B 2203/061* (2013.01); *C01B 2203/062* (2013.01); *C01B 2203/0872* (2013.01); *C01B 2203/1241* (2013.01); *C01B 2203/148* (2013.01); *C10G 2400/02* (2013.01); *C10L 2290/10* (2013.01); *C10L 2290/26* (2013.01); *C10L 2290/42* (2013.01); *C10L 2290/542* (2013.01); *C10L 2290/543* (2013.01); *C10L 2290/545* (2013.01); *Y02E 50/10* (2013.01); *Y02E 50/30* (2013.01); *Y02P 20/10* (2015.11); *Y02P 20/145* (2015.11); *Y02P 30/00* (2015.11)

(58) Field of Classification Search
CPC ......... C10L 2290/542; C10L 2290/545; C10L 2290/543; C10L 2290/26; C10L 2290/42; C10L 2290/10; C01B 32/50; C01B 3/38; C01B 3/50; C01B 3/48; C01B 2203/148; C01B 2203/025; C01B 2203/0233; C01B 2203/062; C01B 2203/0872; C01B 2203/0475; C01B 2203/0405; C01B 2203/043; C01B 2203/1241; C01B 2203/0244; C01B 2203/0283; C01B 2203/061; C12P 7/10; C12P 7/54; C12P 5/023; C12P 7/14; C12P 7/065; C12P 7/06; C07C 29/1518; C07C 31/04; C07C 31/08; C12F 3/10; C10G 2/50; C10G 2400/02; Y02P 20/145; Y02P 20/128; Y02P 30/10; Y02E 50/17; Y02E 50/16; Y02E 50/343

See application file for complete search history.

(56) References Cited

U.S. PATENT DOCUMENTS

| | | | |
|---|---|---|---|
| 5,580,457 A | 12/1996 | Erickson | |
| 5,789,210 A | 8/1998 | Ho et al. | |
| 5,866,382 A | 2/1999 | Hallborn et al. | |
| 6,180,396 B1 | 1/2001 | Ono et al. | |
| 6,475,768 B1 | 11/2002 | Otero et al. | |
| 6,582,944 B1 | 6/2003 | Hallborn et al. | |
| 7,267,774 B2 * | 9/2007 | Peyton ................. | B01D 61/022 203/DIG. 25 |
| 7,285,402 B2 | 10/2007 | Gaddy et al. | |
| 7,309,592 B2 * | 12/2007 | Offerman ................ | C02F 3/346 435/161 |
| 7,497,191 B2 | 3/2009 | Fulton et al. | |
| 7,527,927 B1 | 5/2009 | Ho et al. | |
| 7,527,951 B2 | 5/2009 | Londesborough et al. | |
| 7,622,284 B2 | 11/2009 | Op Den Camp et al. | |
| 7,964,379 B2 | 6/2011 | Verser et al. | |
| 8,080,693 B2 | 12/2011 | Chornet et al. | |
| 8,212,088 B2 | 7/2012 | Olah et al. | |
| 8,236,534 B2 | 8/2012 | Verser et al. | |
| 8,329,436 B2 | 12/2012 | Verser et al. | |
| 8,354,257 B2 | 1/2013 | Datta et al. | |
| 8,383,376 B2 | 2/2013 | Simpson et al. | |
| 8,404,909 B2 | 3/2013 | Jadhav | |
| 8,444,725 B2 * | 5/2013 | Agrawal .................. | C10G 2/32 423/644 |
| 8,507,228 B2 | 8/2013 | Simpson et al. | |
| 8,592,190 B2 | 11/2013 | Gaddy et al. | |
| 8,592,492 B2 | 11/2013 | Chakravarti | |
| 8,647,851 B2 | 2/2014 | Gaddy et al. | |
| 8,658,026 B2 | 2/2014 | Foody et al. | |
| 8,697,405 B2 | 4/2014 | Bell et al. | |
| 8,753,854 B2 | 6/2014 | Foody | |
| 8,759,047 B2 | 6/2014 | Datta et al. | |
| 8,809,015 B2 | 8/2014 | Schultz et al. | |
| 9,034,629 B2 | 5/2015 | Skraly et al. | |
| 9,108,894 B1 | 8/2015 | Foody et al. | |
| 9,476,066 B2 | 10/2016 | Foody | |
| 2003/0111410 A1 | 6/2003 | Branson | |
| 2007/0249029 A1 | 10/2007 | Marshall et al. | |
| 2008/0124775 A1 | 5/2008 | Kovacs et al. | |
| 2009/0151229 A1 | 6/2009 | Rovner | |
| 2010/0076233 A1 | 3/2010 | Cortright et al. | |
| 2010/0105115 A1 | 4/2010 | Simpson et al. | |
| 2010/0298450 A1 | 11/2010 | Datta et al. | |
| 2010/0317074 A1 * | 12/2010 | Simpson .................. | C12P 7/00 435/140 |
| 2011/0138684 A1 | 6/2011 | Kranz | |
| 2011/0177564 A1 | 7/2011 | Stephanopoulos | |
| 2012/0231514 A1 | 9/2012 | Geertman et al. | |
| 2012/0285080 A1 | 11/2012 | Despen et al. | |
| 2012/0323714 A1 | 12/2012 | Saxena | |
| 2013/0078687 A1 | 3/2013 | Hickey et al. | |
| 2013/0078689 A1 | 3/2013 | Hickey | |
| 2013/0078690 A1 | 3/2013 | Reed | |
| 2013/0089905 A1 | 4/2013 | Foody | |
| 2013/0131400 A1 | 5/2013 | Duff et al. | |
| 2013/0143972 A1 | 6/2013 | Townsend et al. | |
| 2013/0143973 A1 | 6/2013 | Townsend et al. | |
| 2013/0144087 A1 | 6/2013 | Arora | |
| 2013/0149693 A1 | 6/2013 | Senaratne et al. | |
| 2013/0149767 A1 | 6/2013 | Marion et al. | |
| 2013/0172633 A1 | 7/2013 | Scates et al. | |
| 2013/0255138 A1 | 10/2013 | Mayeur et al. | |
| 2014/0038252 A1 | 2/2014 | Bell et al. | |
| 2014/0080928 A1 | 3/2014 | Kelfkens et al. | |
| 2014/0165569 A1 | 6/2014 | Hsu | |
| 2014/0227752 A1 | 8/2014 | Datta et al. | |
| 2014/0228598 A1 | 8/2014 | Datta et al. | |
| 2014/0256993 A1 | 9/2014 | Melnichuk et al. | |

(56) References Cited

U.S. PATENT DOCUMENTS

| | | |
|---|---|---|
| 2014/0260311 A1 | 9/2014 | Berlowitz et al. |
| 2017/0130582 A1 | 5/2017 | Hsu |
| 2017/0218404 A1 | 8/2017 | Simpson et al. |

FOREIGN PATENT DOCUMENTS

| | | |
|---|---|---|
| WO | WO 2006113293 A1 | 10/2006 |
| WO | WO 2007117590 A3 | 10/2007 |
| WO | WO 2008041840 A1 | 4/2008 |
| WO | WO 2008098254 A2 | 8/2008 |
| WO | WO 2008157682 A1 | 12/2008 |
| WO | WO 2011000084 A1 | 1/2011 |
| WO | WO 2012003849 A1 | 1/2012 |
| WO | WO 2012062631 A1 | 5/2012 |
| WO | WO 2012/074545 | 6/2012 |
| WO | WO 2010074545 A1 | 6/2012 |
| WO | WO 2012110257 A1 | 8/2012 |
| WO | WO 2013036147 A2 | 3/2013 |
| WO | WO 2013060331 A1 | 5/2013 |
| WO | WO 2013076293 A2 | 5/2013 |
| WO | WO 2013090139 A2 | 6/2013 |
| WO | WO 2013151795 A1 | 10/2013 |
| WO | WO 2016/011554 | 1/2016 |
| WO | WO 2016011555 A1 | 1/2016 |

OTHER PUBLICATIONS

Luong et al. Kinetics of Ethanol Inhibition in Alcohol Fermentation. Biotechnology and Bioengineering (1985), v27, p. 280-285. (Year: 1985).*
Osman et al. Mechanism of Ethanol Inhibition of Fermentation in Zymomonas mobilis CP4. Journal of Bacteriology (1985), v164(1), p. 173-180. (Year: 1985).*
Moulin et al. Inhibition of Alcoholic Fermentation by Substrate and Ethanol. Biotechnology and Bioengineering (1980), v22, p. 2375-2381. (Year: 1980).*
Abdollahi et al., "CO2/CO Separation by Adsorption in Order to Increase CO2 Conversion to CO via RWGS Reaction", University of Ottawa Presentation, (2012).
Abubackar et al., "Biological Conversion of Carbon Monoxide: Rich Syngas or Waste Gases to Bioethanol", Biofuels Bioproducts and Biorefining, vol. 5 (2011) 93-114.
Black et al., Effects of Firing Coal and Biomass Under Oxy-Fuel Conditions in a Power Plant Boiler Using CFD Modelling, Fuel, vol. 113 (2013) 780-786.
Bonaquist, "Analysis of CO2 Emissions, Reductions, and Capture for Large-Scale Hydrogen Production Plants", Praxair, A White Paper, Oct. 2010.
Brooks et al., "Development of a Microchannel in Situ Propellant Production System", Pacific Northwest National Laboratory for US Department of Energy, Contract DE-AC05-76RL01830, PNNL-15456, Sep. 2005.
Brunetti et al., "Membrane Technologies for CO2 Separation", Journal of Membrane Science, vol. 359 (2010) 115-125.
Bustamante et al., "High-Temperature Kinetics of the Homogeneous Reverse Water-Gas Shift Reaction", American Institute of Chemical Engineers, vol. 50, No. 5 (May 2004) 1028-1041.
Butterman et al., "CO2 Enhanced Steam Gasification of Biomass Fuels", Proceedings of 16th Annual North American Waste-to-Energy Conference, Philadelphia PA, May 19-21, 2008.
Centi et al., "Opportunities and Prospects in the Chemical Recycling of Carbon Dioxide to Fuels", Catalysts Today, vol. 148 (2009) 191-205.
Chen et al., "Methanol Synthesis from CO2 Using a Silicone Rubber/Ceramic Composite Membrane Reactor", Separation and Purification Technology, vol. 34 (2004) 227-237.
Datar et al., "Fermentation of Biomass-Generated Producer Gas to Ethanol", Biotechnology and Bioengineering, vol. 86, No. 5 (Jun. 5, 2004) 587-594.

Doty et al., "Toward Efficient Reduction of CO2 to CO for Renewable Fuels", Proceedings of Energy Sustainability 2010, Phoenix, AZ, May 17-22, 2010.
Environmental Protection Agency, "Regulation of Fuels and Fuel Additives: Identification of Additional Qualifying Renewable Fuel Pathways Under the Renewable Fuel Standard Program" Federal Register, vol. 78, No. 43, Mar. 5, 2013, 14190-14217.
Francesconi et al., "Analysis of Design Variables for Water-Gas-Shift Reactors by Model-Based Optimization", Journal of Power Sources, vol. 173 (2007) 467-477.
Genthner et al., "Growth of Eubacterium Limosum with Carbon Monoxide as the Energy Source", Applied and Environmental Microbiology, vol. 43, No. 1 (1982) 70-74.
Global CCS Institute, "Air Products Steam Methane Reformer EOR Project" http://www/globalccsinstitute.com/ project/air-products-steam-methane-reformer-eor-project, Access Date May 12, 2014.
Gomez-Barea et al., "Biomass Gasification Integrated Into a Coal Oxy-Boiler", 19th European Biomass Conference, Berlin, Germany, Jun. 6, 2011.
Green Car Congress, "$12M German Project to Develop Technology for Syngas Production from CO2 and H2; New Hydrogen Production Method", Jul. 2, 2013, www.greencarcongress.com/2013/07/basf-20130702.html, Accessed May 22, 2014.
Green Car Congress, "Algae Species Shows Promise in Reducing Power Plant Pollution and Making Biofuel", Jul. 2, 2013, www.greencarcongress.com/2013/07/coyne-20130702.html, Accessed May 22, 2014.
Green Car Congress, "Algae.Tec Signs Carbon Capture Biofuels Deal with Australia's Largest Coal-Fired Power Company", Jul. 2, 2013, www.greencarcongress.com/2013/07/algaetec-20130702.html, Accessed May 22, 2014.
Haldor Topsoe, "From Solid Fuels to Substitute Natural Fas (SNG) Using TREMP™", Brochure, Mar. 2009.
Hensley, "Catalysts for Mixed Alcohol Synthesis from Biomass Derived Syngas" NREL, CRADA Report, NREL/ TP-7A10-57656, CRD-08-292, Apr. 2013.
Holladay et al., "Microreactor Development for Martian in Situ Propellant Production", Catalysis Today, vol. 120 (2007) 35-44.
Holladay et al., "Compact Reverse Water-Gas-Shift Reactor for Extraterrestrial In Situ Resource Utilization", Journal of Propulsion and Power, vol. 24, No. 3, May-Jun. 2008, 578-582.
Hu et al., "Catalyst Development for Microchannel Reactors for Martian In Situ Propellant Production" Catalysis Today, vol. 125 (2007) 103-110.
IEA-ETSAP et al. "Production of Bio-Methanol" Technology Brief 108, Jan. 2013.
INEOS, "INEOS Bio / Process Technology", Brochure, Apr. 2012.
International Search Report and Written Opinion in PCT Application No. PCT/CA2015/050686, dated Oct. 27, 2015.
Jiang et al., "Turning Carbon Dioxide into Fuel" Philosophical Transactions of the Royal Society A, vol. 368 (2010) 3343-3364.
Joo et al., "CAMERE Process for Methanol Synthesis from CO2 Hydrogenation", Studies in Surface Science and Catalysis, 153 (2004) 67-72.
Joo et al., "Carbon Dioxide Hydrogenation to Form Methanol via a Reverse-Water-Gas-Shift Reaction (the CAMERE Process)", Industrial and Engineering Chemistry Research, vol. 38 (1999), 1808-1812.
Kohn, "Catalytic Reforming of Biogas for Syngas Production", Submission to Columbia University, 2012.
Li et al., "Utilization of Carbon Dioxide from Coal-Fired Power Plant for the Production of Value-Added Products", Submission for Design Engineering of Energy and Geo-Environmental Systems Course (EGEE 580), College of Earth and Mineral Science, Apr. 2006.
Liew et al., "Gas Fermentation for Commercial Biofuels Production", Liquid, Gaseous and Solid Biofuels—Conversion Techniques, Chapter 5 (2013) InTech 125-173.
Luo et al., "Innovative Methods for Biogas Upgrading by the Addition of Hydrogen to Anaerobic Reactor", DTU Environment, Department of Environmental Engineering, Copenhagen, Denmark, Oct. 24-25, 2015.

(56) References Cited

OTHER PUBLICATIONS

Lv et al. "Bio-Syngas Production from Biomass Catalytic Gasification", Energy Conversion and Management, vol. 48 (2007) 1132-1139.

Membrane Technology and Research, Inc. "CO2 Removal from Syngas", Brochure, 2009.

Mohammadi et al., "Kinetic Studies on Fermentative Production of Biofuel from Synthesis Gas Using Clostridium Ljungdahlii", The Scientific World Journal, vol. 2014, Article ID 910590, Jan. 30, 2014.

Morrison, "Production of Ethanol from the Fermentation of Synthesis Gas", Thesis submitted to Mississippi State University, Aug. 2004, 1-143.

Munasinghe et al., "Biomass-Derived Syngas Fermentation into Biofuels: Opportunities and Challenges", Bioresource Technology, vol. 101 (2010) 5013-5022.

Muradov et al., "'Green' Path from Fossil-Based to Hydrogen Economy: An Overview of Carbon-Neutral Technologies", International Journal of Hydrogen Energy, vol. 33 (2008) 6804-6839.

Najafpour et al., "Ethanol and Acetate Synthesis from Waste Gas Using Batch Culture of Clostridium Ljungdahlii", Enzyme and Microbial Technology, vol. 38 (2009) 223-228.

Olah, "Beyond Oili and Gas: The Methanol Economy", Angewandte Chemie International Edition, vol. 44 (2005) 2636-2639.

Olah et al., "Chemical Recycling of Carbon Dioxide to Methanol and Dimethyl Ether: From Greenhouse Gas to Renewable, Environmentally Carbon Neutral Fuels and Synthetic Hydrocarbons", Journal of Organic Chemistry, vol. 74 (2009) 487-498.

Park et al., "Development of ZnO/Al2O3 Catalyst for Reverse-Water-Gas-Shift Reaction of CAMERE (carbon dioxide hydrogenation to form methanol via a reverse-water-gas-shift reaction) Process", Applied Catalysis A: General, vol. 211 (2001) 81-90.

Peer et al., "Separation of Hydrogen from Carbon Monoxide Using a Hollow Fiber Polyimide Membrane: Experimental and Simulation", Chemical Engineering Technology, vol. 30, No. 10 (2007) 1418-1425.

Phillips et al., "Synthesis Gas as Substrate for the Biological Production of Fuels and Chemicals", Applied Biochemistry and Biotechnology, vol. 45/46 (1994) 145-157.

Regalbuto, "An NSF Perspective on Next Generation Hydrocarbon Biorefineries", Computers and Chemical Engineering, vol. 34 (2010) 1393-1396.

Richter et al., "A Two-Stage Continuous Fermentation System for Conversion of Syngas into Ethanol", Energies, vol. 6 (2013) 3987-4000.

Ryden et al., "Using Steam Reforming to Produce Hydrogen with Carbon Dioxide Capture by Chemical-Looping Combustion", International Journal of Hydrogen Energy, vol. 31 (2006) 1271-1283.

Schultz et al., "Synthesis of Hydrocarbon Fuels Using Renewable and Nuclear Energy", American Nuclear Society, vol. 166, No. 1 (2009) 56-63.

Schultz et al., "Hydrogen and Synthetic Hydrocarbon Fuels—A Natural Synergy", National Hydrogen Association Annual Meeting Longbeach, CA, Mar. 13-16, 2006.

Serrano-Ruiz et al., "Catalytic Routes for the Conversion of Biomass into Liquid Hydrocarbon Transportation Fuels", Energy & Environmental Science, vol. 4 (2011) p. 83-89.

Shelley, "Capturing CO2: Membrane Systems Move Forward", Chemical Engineering Progress, vol. 105, No. 4 (Apr. 2009) 42-47.

Shen et al., "Chemical Fixation of Carbon Dioxide Catalyzed by Binaphthyldiamino Zn, Cu, and Co Salen-Type Complexes", Journal of Organic Chemistry, vol. 68 (2003) 1559-1562.

Spath et al., "Life Cycle Assessment of Hydrogen Production via Natural Gas Steam Reforming", National Renewable Energy Laboratory, NREL/TP-570-27637, Feb. 2001.

Spivey et al., "Heterogeneous Catalytic Synthesis of Ethanol from Biomass-Derived Syngas", Chemical Society Reviews, vol. 36 (2007) 1514-1528.

Subramani et al., "A Review of Recent Literature to Search for an Efficient Catalytic Process for the Conversion of Syngas to Ethanol", Energy & Fuels, vol. 22 (2008) 814-839.

Sun et al., "In Situ IR Studies on the Mechanism of Methanol Synthesis over an Ultrafine Cu/ZnO/Al2O3 Catalyst", Applied Catalysis A: General, vol. 171 (1998) 301-308.

Toftegaard, "OxyFuel Combustion of Coal and Biomass", Ph.D. Thesis submitted to Technical University of Denmark and DONG Energy Power, Mar. 31, 2001.

Vanhassel et al. "Advanced Oxy-fuel Boilers for Cost-Effective CO2 Capture", Praxair Presentation, Fourth Annual Conference on Carbon Capture & Sequestration, May 2-5, 2005.

Walton et al., "A Novel Adsorption Cycle for CO2 Recovery: Experimental and Theoretical Investigations of a Temperature Swing Compression Process", Separation Science and Technology, vol. 41 (2006) 485-500.

Wang et al., "Methanation of Carbon Dioxide: An Overview", Frontiers of Chemical Science and Engineering, vol. 5, No. 1 (2011) 2-10.

Wang et al., "Recent Advances in Catalytic Hydrogenation of Carbon Dioxide", Chemical Society Reviews, vol. 40 (2011) 3703-3727.

Wang et al., "Reverse Water Gas Shift Reaction Over Co-precipitated Ni—CeO2 Catalysts", Journal of Rare Earths, vol. 26 (2008) 66-70.

Wikipedia, "Electrochemical Reduction of Carbon Dioxide" http:/en.wikipedia.org/wiki/Electrochemical_reduction_of_carbon_dioxide, Access date: May 12, 2014.

Wikipedia, "Green Methanol Synthesis", http:/en.wikipedia.org/wiki/Green_Methanol_Synthesis, Access date: May 9, 2014.

Xu et al., "Adding Value to Carbon Dioxide from Ethanol Fermentations", Bioresource Technology, vol. 101 (2010) 3311-3319.

Environmental Protection Agency, "Deferral for CO2 Emissions from Bioenergy and Other Biogenic Sources Under the Prevention of Significant Deterioration (PSD) and Title V Programs", Federal Register, vol. 76, No. 139 (Jul. 20, 2011).

International Search Report and Written Opinion in International Application No. PCT/CA2015/050687, dated Oct. 23, 2015.

Al-Hasan, M., Effect of ethanol-unleaded gasoline blends on engine performance and exhaust emission. Energy Conversion and Management (2003), v44(9), p. 1547-61.

Canilha et al. Bioconversion of Sugarcane Biomass into Ethanol: An Overview about Composition, Pretreatment Methods, Detoxification of Hydrolysates, Enzymatic Saccharification, and Ethanol Fermentation. Journal of Biomedicine and Biotechnology (2012), Article ID 989572, 12 pages (2012).

Costa et al. Growth Inhibition Kinetics for the Acetone-Butanol Fermentation. Foundations of Biochemical Engineering (1983) Ch 24, p. 501-512 (1983).

Kundiyana et al. Syngas fermentation in a 100L pilot scale fermentor: Design and process considerations. Journal of Bioscience and Bioengineering (2010), v105(5) p. 492-98.

Luong et al. Kinetics of Ethanol Inhibition in Alcohol Fermentation. Biotechnology and Bioengineering (1985), v27, p. 280-285 (1985).

Mayank et al. Mathematical Models of ABE fermentation: review and analysis. Critical Reviews in Biotechnology (2013) V33(4), p. 419-447 (2013).

Moulin et al. Inhibition of Alcoholic Fermentation by Substrate and Ethanol. Biotechnology and Bioengineering (1980), v22, p. 2375-2381 (1980).

Osman et al. Mechanism of Ethanol Inhibition of Fermentation in Zymomonas mobilis CP4. Journal of Bacteriology (1985), v164(1), p. 173-180 (1985).

Corn Steep Liquor—Technical Evaluation Report. USDA National Organic Program. 8 pages (2010).

Brazilian Application No. BR112017001208-1 Office Action dated Dec. 4, 2019.

Casey et al., "Effect of acetic acid and pH on the cofermentation of glucose and xylose to ethanol by a genetically engineered strain of *Saccharomyces cerevisiae*", FEMS Yeast (2010), 10, 385-393. (Year: 2010).

(56) References Cited

OTHER PUBLICATIONS

Steinbusch et al. Selective inhibition of methanogenesis to enhance ethanol and n-butyrate production through acetate reduction in mixed culture fermentation. Bioresource Technology (2009), 100, 3261-3267. (Year: 2009).

Worden et al. Engineering Issues in Synthesis-Gas Fermentations. Chapter 18 in Fuels and Chemicals from Biomass (1997), ISBN: 0841235082, Saha and Woodward (Eds), ACS Symposium Series, pp. 320-335. (Year: 1997).

Zigova and Sturdik, "Advances in biotechnological production of butyric acid", Journal of Industrial Microbiology & Biotechnology ( 2000), 24, 153-160. (Year: 2000).

Office Action issued in U.S. Appl. No. 16/244,756 dated May 19, 2020.

* cited by examiner

PROCESS FOR PRODUCING FUEL USING TWO FERMENTATIONS

This application is a continuation of U.S. application Ser. No. 15/327,348 filed Jan. 18, 2017, which is a national stage application of PCT/CA2015/050687 having an international filing date of Jul. 22, 2015, which claims benefit of U.S. provisional application No. 62/027,370 filed Jul. 22, 2014, U.S. provisional application No. 62/115,273 filed Feb. 12, 2015, and U.S. patent application Ser. No. 14/563,116 filed Dec. 8, 2014, now U.S. Pat. No. 9,108,894, each of which is incorporated by reference herein in its entirety.

TECHNICAL FIELD

The present invention relates to a process for producing a fermentation product, and in particular to a process for producing a fuel and/or fuel intermediate using two fermentations.

BACKGROUND

The majority of the energy used today is derived from fossil fuels, despite the on-going controversy surrounding their environmental impact. Fossil fuels, as with any carbon-containing materials, release carbon dioxide upon their combustion. The extraction of fossil fuels for energy production results in the release of carbon into the atmosphere that was previously stored in the earth, and thereby has a net effect of increasing the levels of atmospheric carbon dioxide. A major source of atmospheric fossil carbon dioxide comes from "tailpipe emissions" from cars and carbon dioxide-containing flue gases from fossil fuel burning power plants.

On the other hand, carbon dioxide released from combusting fuel derived from non-fossil organic material is relatively benign, given that it simply returns to the atmosphere carbon that was recently fixed by photosynthesis. More generally, this relatively benign nature is also true of carbon dioxide released as a byproduct from the processing of non-fossil organic material during fermentation or other processes that break down organic material into simpler molecules. Carbon dioxide sourced from non-fossil organic material is referred to herein as biogenic carbon dioxide, as described below. Fuels or fuel intermediates containing biogenic carbon are known as "biofuels" or "biofuel intermediates" and the tailpipe emissions from biofuels are generally considered benign to the atmosphere.

Displacing fossil-based fuel with fuel made from non-fossil organic material creates atmospheric greenhouse gas (GHG) benefits by displacing carbon dioxide emissions that would have been from the fossil fuel and would have led to an increase in atmospheric levels of carbon dioxide. Carbon dioxide is a greenhouse gas and has been identified as a contributor to global climate change. Various governments have promoted the increased use of renewable fuel through legislative and regulatory regimes, including the Energy Independence and Security Act (EISA) in the U.S. Some of the purposes of the EISA are to increase the production of clean renewable fuels, to promote research on and deploy GHG capture, and to reduce fossil fuels present in transportation fuels. In addition to EISA, numerous jurisdictions, such as the state of California, the province of British Columbia, Canada and the European Union, have set annual targets for reduction in average life cycle GHG emissions of transportation fuel. Such an approach is often referred to as a Low Carbon Fuel Standard ("LCFS"), where credits may be generated for the use of fuels that have lower life cycle GHG emissions than a specific baseline fuel.

Despite these government incentives, biofuels still do not enjoy widespread use due to technical and cost limitations. One challenge with commercializing biofuels is that the yield of fuel from the starting material is often low. A variety of factors contribute to these low yields. For example, in the fermentative production of ethanol from non-fossil organic material, such as corn, a significant amount of the carbon from the sugar is not converted into fuel product. During fermentation, the yeast produces carbon dioxide in addition to the desired ethanol product. From one mole of glucose, two moles of each ethanol and carbon dioxide are produced. This carbon is usually not captured as the carbon dioxide is typically vented to atmosphere due to its low energy value and, given that the carbon dioxide is biogenic, it has no net effect on the life cycle GHG emissions of the ethanol. Another issue is the cost and GHG emissions associated with purifying the ethanol product.

Moreover, only the carbohydrate-rich portion of organic material, such as grain or the stalks of sugar cane, is readily converted to ethanol. While the production of fuel from these parts of the plant can be carried out with relative ease, the structural parts of the plant also contain sugar in the form of cellulose and hemicellulose, which is generally more difficult to convert to biofuel. Since these parts of the plant are not converted to product in such fuel fermentation processes, this represents a significant yield loss.

Research efforts have been directed toward the development of processes that can convert the non-edible cellulose and hemicellulose portion of plant material to fuels. A first chemical processing step for converting non-edible parts of plants to ethanol, or other fermentation products, involves breaking down the fibrous material to liberate sugar monomers from the plant material. This can be achieved by hydrolyzing the hemicellulose first to its constituent sugars, using a chemical such as sulfuric acid, followed by hydrolysis of the cellulose to glucose by enzymes referred to as cellulase enzymes. These sugars are then fermented to ethanol with yeast or bacteria. A non-sugar containing component that remains after the conversion, known as lignin, can be burned to generate heat and power for internal plant operations. Thus, the process benefits from maximizing the whole plant for fuel or energy production. Nonetheless, there are challenges in obtaining a high yield of sugar for subsequent fermentation due to the recalcitrance of the cellulose to enzymatic hydrolysis. Although there is on-going research aimed at improving the efficiency of this step, progress is slow and the process is still costly.

Another approach for utilizing the whole plant involves subjecting the organic material to gasification to make syngas, which is composed of carbon monoxide, hydrogen and typically carbon dioxide. Syngas can then be used as a precursor to make additional chemicals or used as a fuel itself. While the whole plant, including both the carbohydrate and lignin components, can be converted to syngas, some of the energy stored in the sugar polymers is lost in the process. Moreover, many side products are produced, including tars and carbon dioxide which are not converted to fuel and thus contribute to yield loss.

SUMMARY

In accordance with one embodiment, a process for making fuels or fuel intermediates from non-fossil organic material is provided that improves product yield from non-fossil organic material and/or maintains a beneficial GHG emission impact. The process involves two fermentations including a first fermentation that includes the fermentation of one or more gases (e.g., CO, $CO_2$, and/or $H_2$) to provide a fermentation product and a second fermentation that includes the fermentation of one or more carbohydrates (e.g., glucose, xylose, sucrose, fructose, etc) to a fermentation product. In one embodiment, the fermentation products from the first and second fermentations, which may be run simultaneously or sequentially, and which may be operated in batch or continuous mode, are used to produce a same fuel and/or fuel intermediate, such that when an aqueous stream comprising the gas fermentation product is introduced into carbohydrate fermentation process or at a step upstream of the carbohydrate fermentation, the concentration of the fermentation product in the carbohydrate fermentation unit increases. This increase in concentration reduces the recovery costs of the aggregate fermentation product. In one embodiment, the one or more gases provided to the gas fermentation are biogenic and obtained from the carbohydrate fermentation, thus providing increased yield of biofuel and/or biofuel intermediates for a given amount of carbohydrate feedstock.

In accordance with an aspect of the invention there is provided a process for producing a fermentation product comprising: introducing a first substrate to a first fermentation unit to produce a first fermentation product, the first substrate comprising at least one compound selected from the group consisting of carbon monoxide, carbon dioxide, and hydrogen; introducing a second substrate to a second fermentation unit to produce a second fermentation product, the second substrate comprising at least one carbohydrate derived from organic material in one or more processing steps, the first fermentation product the same as the second fermentation product; introducing an aqueous stream comprising the first fermentation product to the process such that at least a portion of the first fermentation product enters the second fermentation unit; and recovering at least a portion of the first and second fermentation products from the effluent of the second fermentation unit to provide the fermentation product.

In accordance with an aspect of the invention there is provided a process for producing ethanol comprising: introducing a first substrate to a first fermentation unit to produce a broth including ethanol, the first substrate comprising at least one compound selected from the group consisting of carbon monoxide, carbon dioxide, and hydrogen; removing cells from at least a portion of the broth to provide an aqueous stream comprising ethanol; introducing a second substrate to a second fermentation unit to produce a broth including ethanol, the second substrate comprising at least one carbohydrate derived from organic material in one or more processing steps; introducing at least a portion of the aqueous stream comprising ethanol to the process such that at least a portion of the ethanol in the aqueous stream enters the second fermentation unit, and such that a concentration of ethanol exiting the second fermentation unit is greater than a concentration of ethanol in the aqueous stream; and recovering ethanol from the second fermentation unit, wherein the recovered ethanol comprises ethanol produced in the first and second fermentation units.

In accordance with an aspect of the invention there is provided a process for producing a fermentation product comprising: fermenting at least one gas in a gas fermentation to produce a first fermentation product, the at least one gas comprising at least one of carbon monoxide, carbon dioxide, and hydrogen; fermenting at least one carbohydrate in a carbohydrate fermentation to produce a second fermentation product, the second fermentation product the same as the first fermentation product, the at least one carbohydrate derived from organic material processed in one or more processing steps and comprising a sugar, a starch, or a combination thereof; combining an aqueous stream comprising the first fermentation product and originating from the first fermentation with a stream comprising the carbohydrate, the organic material, processed organic material, or a combination thereof such that at least a portion of the first fermentation product enters the second fermentation unit; and recovering the first and second fermentation products from the carbohydrate fermentation, wherein the aqueous stream is fed to a stage of the process requiring an addition of water.

In accordance with an aspect of the invention there is provided process for producing ethanol comprising: conducting a gas fermentation that includes introducing at least one gas selected from the group consisting of carbon monoxide, carbon dioxide, and hydrogen gas to a gas fermentation unit; feeding a gas stream comprising biogenic carbon dioxide to the gas fermentation unit, the biogenic carbon dioxide sourced from an ethanol production process, the ethanol production process comprising a carbohydrate fermentation that includes introducing at least one carbohydrate to a carbohydrate fermentation unit; and providing an aqueous stream comprising ethanol produced from the gas fermentation or derived from an intermediate produced by the gas fermentation for introduction into the ethanol production process at a stage that allows at least a portion of the ethanol in the aqueous stream to enter the carbohydrate fermentation unit.

In accordance with an aspect of the invention there is provided a process for producing ethanol comprising: receiving an aqueous stream comprising ethanol derived from biogenic carbon dioxide introduced into a gas fermentation unit; introducing at least a portion of the aqueous stream into an ethanol production process such that at least a portion of the ethanol in the aqueous stream enters a carbohydrate fermentation unit in the ethanol production process, the carbohydrate fermentation unit for producing ethanol derived from at least one carbohydrate; providing biogenic carbon dioxide generated in the ethanol production process to a production plant for introduction into the gas fermentation unit; and recovering ethanol from the carbohydrate fermentation unit, the recovered ethanol including ethanol derived from the biogenic carbon dioxide introduced to the gas fermentation unit and ethanol derived from the at least one carbohydrate introduced to the carbohydrate fermentation unit.

In accordance with an aspect of the invention there is provided a process for producing ethanol comprising: receiving biogenic carbon dioxide generated in an ethanol production process; introducing the biogenic carbon dioxide into a gas fermentation unit and producing ethanol derived from the biogenic carbon dioxide introduced into the gas fermentation unit; providing an aqueous stream comprising the ethanol derived from the biogenic carbon dioxide to the ethanol production process, the aqueous stream for introduction into the ethanol production process such that at least a portion of the ethanol in the aqueous stream enters a carbohydrate fermentation unit for producing ethanol derived from at least one carbohydrate introduced into the carbohydrate fermentation unit, the ethanol production process including a step of recovering ethanol from the carbohydrate fermentation unit, the recovered ethanol including ethanol derived from the biogenic carbon dioxide introduced into the gas fermentation unit and ethanol derived from the at least one carbohydrate introduced into the carbohydrate fermentation unit.

BRIEF DESCRIPTION OF THE FIGURES

Exemplary embodiments will now be described in conjunction with the drawings in which.

It will be noted that throughout the appended drawings, like features are identified by like reference numerals.

DETAILED DESCRIPTION

Definitions

Figure 1:
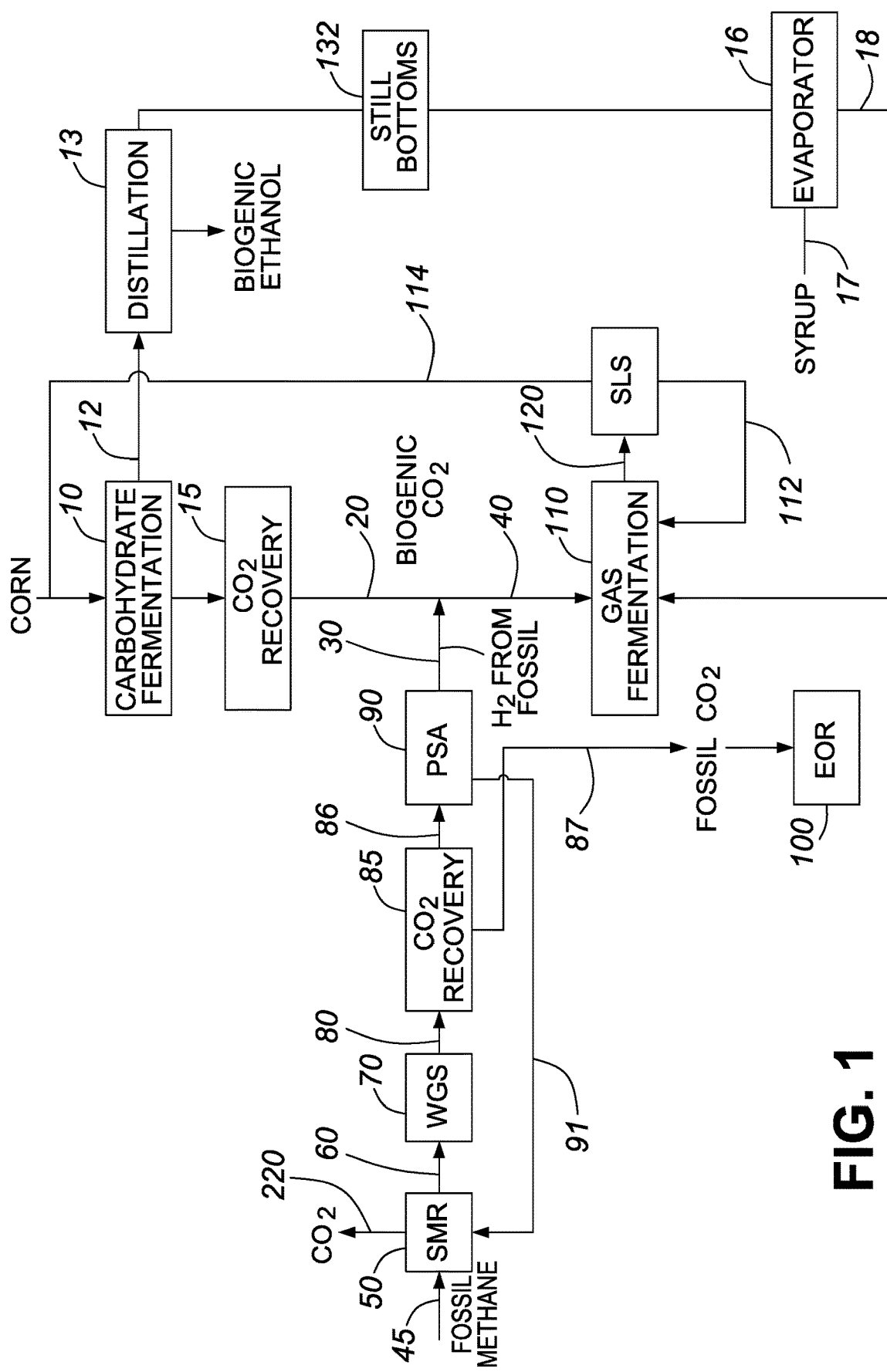
FIG. 1 is a process flow diagram showing the production of biogenic ethanol in accordance with one embodiment of the invention.

The term "biogenic carbon-based" in reference to a product, such as a fuel, fuel intermediate or a chemical product, means that the product comprises carbon that is sourced directly or indirectly from non-fossil organic material. This can include carbon derived from fossil carbon dioxide, or from both fossil and non-fossil carbon dioxide, but that is considered biogenic by those skilled in the art, as described further herein.

As used herein, the term "non-fossil organic material" or simply "organic material" refers to a material comprising carbon from one or more biologic sources that is not obtained from underground geologic formations. Any suitable non-fossil, biologic source material obtained or derived directly or indirectly from plants or animals can be used as the organic material in various embodiments of the process to provide a carbon and/or energy source. This includes plant derived organic material comprising polysaccharides, including starch, cellulose and hemicellulose, oligosaccharides, disaccharides, monosaccharides, or a combination thereof. Other biologic, non-fossil source material that can be utilized as a carbon and/or energy source includes compounds or molecules derived from non-sugar containing material, such as lignin and fats. The organic material may be in liquid form containing soluble components, solid form, gaseous form, or any combination thereof. For example, organic material may include material comprising starches, sugars or other carbohydrates derived from sugar or starch crops. The sugar or starch crops may include, but are not limited to, corn, wheat, barley, rye, sorghum, rice, potato, cassava, sugar beet, sugar cane, or a combination thereof.

The organic material may also be biomass or biomass derived material. Examples of biomass and biomass derived material include (i) energy crops; (ii) residues, byproducts or waste from the processing of plant material in a facility, or feedstock derived therefrom; (iii) agricultural residues; (iv) forestry material; (v) material derived from pulp and paper processing; (vi) pulp and paper residues; and (vii) municipal waste or components removed or derived from municipal waste. The biomass or biomass derived material can be in any form, including solid, liquid, gaseous form, or a combination thereof.

Energy crops include biomass crops such as grasses, including C4 grasses, such as switch grass, energy cane, sorghum, cord grass, rye grass, *miscanthus*, reed canary grass, C3 grasses such as *Arundo donax* or a combination thereof.

Residues, byproducts or waste from the processing of plant material in a facility or feedstock derived therefrom include residues remaining after obtaining sugar from plant biomass such as sugar cane bagasse, sugar cane tops and/or leaves, beet pulp, or residues remaining after removing sugar from Jerusalem artichoke or residues remaining after grain processing, such as corn fiber, corn stover or bran from grains. Agricultural residues include, but are not limited to soybean stover, corn stover, rice straw, sugar cane tops and/or leaves, rice hulls, barley straw, corn cobs, wheat straw, canola straw, oat straw, oat hulls or corn cobs.

Forestry material includes any species of hardwood or softwood. The term includes residues, byproducts, waste or non-waste material from processing any hardwood or softwood species. Examples of waste include residues from sawmills, trimmings or slash from logging operations. Pulp and paper residue, includes non-pulp and non-paper products from chemical pulping or paper making such as black liquor, spent sulfite liquor, sludge, broke, fines or precipitated lignin.

Municipal waste includes post-consumer material or waste from a variety of sources, such as domestic, commercial, institutional and industrial sources. For example, the term includes refuse from waste collection, raw sewage and sewage sludge.

Biomass or biomass derived material can be a mixture of fibers that originate from different kinds of plant material, including mixtures of cellulosic and non-cellulosic biomass. In addition, the biomass may comprise fresh biomass, partially dried biomass, fully dried biomass, or a combination thereof. Moreover, new biomass varieties may be produced from any of those listed above by plant breeding or by genetic engineering.

The term "energy product", as used herein, may refer to (i) any product that is used to generate electrical energy or heat, such as lignin or methane; and/or (ii) products that store heat energy or electrical energy including steam and electricity produced by combusting non-fossil organic material.

A "fuel" includes liquid or gaseous material, which may contain carbon, that can be combusted to produce power or heat and includes both transportation and heating fuel. The fuel may be a liquid at 20° C., such as an alcohol, or a gaseous fuel, such as methane or hydrogen, which are gases at this temperature. The fuel may exist in any form, including gaseous, liquid or compressed form.

A "fuel intermediate" is a precursor used to produce a fuel by a further conversion process, such as by a biologic conversion, a chemical conversion, or a combination thereof.

A "chemical product" is a chemical compound used in a production process or a product such as a commodity. Some examples of chemical products produced from non-fossil organic material are sugar acids, sugar alcohols, organic acids, bioplastic or bioplastic intermediates, fermentation-derived chemicals, fertilizer and lignin-based products. A "lignin-based product" is a product that comprises lignin, a lignin derivative, or a product that is produced from lignin.

A "biofuel" or a "biofuel intermediate" refers to a fuel and fuel intermediate, respectively, containing biogenic carbon. One example of a biogenic carbon-based fuel is bioethanol (e.g., ethanol containing biogenic carbon).

Some examples of fuels, fuel intermediates, chemical and energy products, and processes for their production from non-fossil organic material are described below. Such processes include fermentation to produce fermentation products, or thermal processes, including combustion, gasification, pyrolysis or a combination thereof.

As used herein, the term "fermentation" includes the biologic conversion of organic material or carbon-containing materials derived from underground geological formations by any process using microbes (e.g., bacteria, yeast, or other microorganisms) in one or more stages to a fermentation product. The organic material may be in any form, including solid, liquid, or gaseous forms, or any combination thereof. The microbes, which may also be referred to as biocatalysts, perform the chemical transformation on the fermentation substrate to produce the fermentation products. The fermentation substrate, which includes the molecules that are chemically transformed, typically includes organic compounds. The microbes, also referred to herein as the microorganisms, are typically provided in a fermentation unit. The fermentation unit typically includes a container for holding the fermentation broth, which is a mixture typically including the substrates, the microorganisms, nutrients, solvents, diluents, fermentation products, etc. The fermentation broth may include solids, liquids, and/or gases. The fermentation unit, which may also be termed a fermentor or bioreactor, may be an anaerobic digester, a gas fermentor, or a conventional yeast fermentation reactor. The fermentation unit may include one or more fermentation tanks, each of which may include agitation means, a sterilization system, gas feeds, liquid nutrient feeds, temperature control, and/or pH control. For example, a fermentation unit may include a series of bioreactors including a growth bioreactor, and one or more fermentation tanks for different fermentation stages. Some or all of the fermentation broth may be subject to a solid liquid separation that provides a stream having a relatively high concentration of fermentation product and a stream having a relatively high concentration of microorganisms. Reintroducing the microorganisms back into the fermentation tank, also known as cell recycle, may reduce costs (e.g., since some microorganisms may be expensive). Moreover, since microorganisms such as yeast act as self-reproducing biocatalysts, reintroducing the microorganisms back into the fermentation may allow the microorganisms to adapt and/or the fermentation process to optimize. Fermentation products may be recovered (e.g., separated and/or purified) from the fermentation broth using any of the methods known in the art (e.g., distillation, adsorption, chromatography, membrane separation, etc.). Some examples of products and/or byproducts produced by fermentation include ethanol, butanol, lactic acid, acetic acid, butyric acid, acetone, carbon dioxide and hydrogen gas ($H_2$). The term "fermentation product" as used herein refers to alcohols and/or acids produced by fermentation. Processes comprising fermentation may also generate one or more energy products such as lignin, methane, steam or electricity for internal and/or external use.

Carbohydrate Fermentation

In general, the most common substrates for fermentation are carbohydrates (i.e., saccharides), which include sugars, starch and cellulose. In one embodiment, the carbohydrates are obtained from biomass. In one embodiment, the carbohydrates are obtained from organic material that may be food crops. Some examples of product and/or byproducts produced during the fermentation of sugars such as glucose include ethanol, lactic acid, acetic acid, carbon dioxide ($CO_2$), and hydrogen ($H_2$).

For example, in the production of ethanol, the fermentation of glucose produces two molecules of carbon dioxide by the following reaction:

$$C_6H_{12}O_6 \rightarrow 2C_2H_6O + 2CO_2.$$

The carbon dioxide generated during fermentations may be collected using known processes as discussed further herein.

When the carbohydrate is obtained from feedstock derived from plants or plant-based materials, the feedstock may be subjected to a pretreatment and/or hydrolysis prior to fermentation. In general, the pretreatment and/or hydrolysis may include various mechanical, chemical, thermal and/or biologic processes to provide more biogenic carbon-based sugars from the feedstock and/or to allow more of the biogenic carbon-based carbohydrate to be fermented.

In one embodiment, the feedstock includes a sugar or starch crop. For a sugar crop, the non-fossil organic material is typically processed to extract sugar therefrom. The sugar may be subsequently fermented in the carbohydrate fermentation. Sugar crops, including, but not limited to, sugar cane, sugar beets or sweet sorghum, may be subjected to a mechanical treatment, such as crushing and/or pressing, to extract the sugar from the plants. For example, sucrose from sugar cane can be extracted using roller mills. Sugar from sweet sorghum stalks can be extracted in a similar manner, although certain varieties of sorghum contain grain that can be processed using technology employed for processing starch crops as described below.

Starch crops, which include cereal crops, may be subjected to size reduction, such as by milling or grinding. The starch may be subsequently hydrolyzed with enzymes, by chemical treatment, or a combination of these treatments. By way of example, grain may be milled with a roller or hammer mill, followed by the addition of water and hydrolysis of the starch with amylases to produce fermentable sugar. This method is commonly referred to as "dry milling". An alternative method is "wet milling" in which the grain is steeped, such as in an acidic solution and/or a solution containing enzymes, and then subjected to size reduction, such as milling, to facilitate separation of the starch from the other components of the grain. The starch is subsequently hydrolyzed to sugar using methods described above.

In one embodiment, the feedstock includes a cellulosic material. Cellulosic feedstock typically includes lignocellulose, which is a structural material composed mainly of cellulose, hemicellulose, and lignin. Processing a cellulosic feedstock and/or a feedstock that includes cellulose may include pretreating the biomass or biomass derived material to disrupt fiber structure. For example, in one embodiment, the feedstock including cellulose is subject to a pretreatment and/or hydrolysis that liberates glucose and/or hemicellulose for the fermentation step. Pretreatment and/or hydrolysis may include heat, mechanical processing, addition of one or more chemicals, biocatalysts, or combinations thereof to release sugars. In one embodiment, pretreatment hydrolyzes between 30 wt % and 100 wt % of the xylan from the hemicellulose. In other embodiments, pretreatment provides more limited xylan hydrolysis.

Sugars released during the pretreatment and/or hydrolysis, may then be subject to the fermentation to provide one or more biofuels, biofuel intermediates, and/or chemical product. In general, some of the lignin may remain insoluble and will not be converted to the one or more biofuels, biofuel intermediates, and/or chemical products resulting from the fermentation. For example, in one embodiment, between 10 wt % and 100 wt % of the lignin may remain insoluble. The insoluble lignin may be used to generate an energy product or chemical product. For example, in one embodiment, the lignin is subject to a conversion process to generate an energy product (e.g., heat or power). The energy product produced from the lignin can be used to displace fossil energy by use within the production process itself, or by exporting the energy product, such as to supply energy in the form of electricity to the grid. Recovered lignin may also be utilized for making a chemical product, such as lignin-based product. The lignin-based product may be an additive in a commercial application, a dispersant, a binder or an adhesive. One example of a conversion process is heating lignin at elevated temperature in a gasification or pyrolysis process to produce aromatic compounds such as phenols.

Non-limiting examples of pretreatment include acid pretreatment, alkali pretreatment and hydrothermal pretreatment. Such pretreatment processes are set forth in U.S. Application No. 61/948,726 filed Mar. 6, 2014, which is incorporated herein by reference.

The pretreatment may improve the accessibility of cellulose to a subsequent enzymatic or chemical hydrolysis to convert cellulose to glucose. The enzymatic hydrolysis may involve the addition of enzymes including cellulases and hemicellulases. Other enzymes that may be used include amylases, glucanases, proteases, lipases, pectinases, laccases, phytases or combinations thereof. The glucose may then be converted to one or more fermentation products via at least one fermentation process.

In one embodiment, the fermentation produces a liquid biofuel, biofuel intermediate, and/or a chemical product. For example, in one embodiment the fermentation produces and/or provides an alcohol, such as ethanol, propanol, butanol and isobutanol. For ethanol production, the fermentation can be carried out with a yeast or a bacterial strain, such as a *Saccharomyces* spp. or *Zymomonas mobilis* strain. Butanol may be produced from glucose by a microorganism such as *Clostridium acetobutylicum* and then concentrated by distillation. The alcohol may then be distilled to obtain a concentrated ethanol solution.

Xylose, arabinose and other sugars that are derived from the hemicelluloses may also be fermented to fuels, fuel intermediates or chemical products. An example of a fuel is ethanol, which can be produced by a yeast strain that naturally contains, or has been engineered to contain, the ability to ferment these sugars to ethanol. Non-limiting examples of microbes that have been genetically modified to ferment xylose include recombinant *Saccharomyces* strains into which has been inserted either (a) the xylose reductase (XR) and xylitol dehydrogenase (XDH) genes from *Pichia stipitis* (see for example U.S. Pat. Nos. 5,789,210, 5,866, 382, 6,582,944 and 7,527,927 and European Patent No. 450530) or (b) fungal or bacterial xylose isomerase (XI) gene (see for example U.S. Pat. Nos. 6,475,768 and 7,622, 284). Examples of yeasts that have been genetically modified to ferment L-arabinose include, but are not limited to, recombinant *Saccharomyces* strains into which genes from either fungal (see for example U.S. Pat. No. 7,527,951) or bacterial (see for example WO 2008/041840) arabinose metabolic pathways have been inserted.

Some examples of chemical products that can be produced by fermentation include sugar acids including xylonic acid and arabonic acid; sugar alcohols including xylitol, arabitol, erythritol, galactitol and mannitol; and organic acids including adipic acid, citric acid, malic acid, succinic acid, pyruvic acid, acetic acid, itaconic acid and lactic acid; biooils including sesquiterpenes such as farnesene; diols, including butanediol and 1,3 propanediol; alcohols, such as propanol; and ketones, including acetone. Examples of processes for producing such chemical products by fermentation from organic material are set forth in U.S. Publication No. 2012/0231514 (published Sep. 13, 2012).

In one embodiment, the carbohydrate fermentation is an anaerobic digestion (e.g., which involves the biologic breakdown of non-fossil organic material by microorganisms generally under low oxygen conditions, or in the absence of oxygen, to produce gases). Prior to anaerobic digestion, the non-fossil organic material is optionally processed by mechanical, chemical, thermal and/or biologic processes to improve its ability to be fermented. Biologic processes include treatment with enzymes including cellulases, hemicellulases, amylases, glucanases, proteases, lipases, pectinases, laccases, phytases or combinations thereof.

The gases produced by anaerobic digestion of non-fossil organic material include methane, biogenic carbon dioxide, and hydrogen sulfide. As would be appreciated by those skilled in the art, anaerobic digestion may involve the decomposition of non-fossil organic material, including carbohydrates, fats and proteins therein, into simple sugars and glycerol. These compounds may then be converted to acids, which are subsequently converted into methane by methanogenic bacteria or other microorganisms, typically by the following reaction:

$$C_6H_2O_6 \rightarrow 3CH_4 + 3CO_2.$$

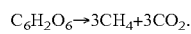

The gases from anaerobic digestion, also referred to herein as "crude biogas" or simply as "biogas", include methane, carbon dioxide and typically one or more impurities such as hydrogen sulfide and/or siloxanes. Generally, after collection of carbon dioxide, and removal of one or more impurities, the methane can be used as compressed natural gas or liquid natural gas to power vehicles and/or may be used for heating. Alternatively, the methane from biogas can be used to produce another fuel, fuel intermediate and/or chemical product.

Gas Fermentation

While carbohydrate substrates derived from food crops and/or biomass have been and continue to be important in producing biofuels and/or biofuel intermediates, there has been growing interest in gas fermentation. For example, there has been increased interest in the use of syngas and/or industrial waste streams as feedstock to produce biofuels and/or other high value products. In terms of producing biofuels and/or biofuel intermediates, substrates that include biogenic carbon monoxide and/or biogenic carbon dioxide are of particular interest. In general, the substrates may also include hydrogen gas (e.g., fossil derived hydrogen gas).

In gas fermentation, the substrate typically includes one or more gases containing carbon (e.g., fossil or biogenic carbon). For example, in one embodiment, the substrate for gas fermentation is a CO rich stream (biogenic or fossil). In one embodiment, the substrate for gas fermentation is syngas (biogenic or fossil). In one embodiment, the substrate for gas fermentation includes or is derived from carbon dioxide (biogenic or fossil) and hydrogen gas.

For example, in one embodiment, gas fermentation may involve the conversion of a gaseous stream containing biogenic carbon dioxide and/or biogenic carbon monoxide to a fuel, fuel intermediate and/or chemical product. Some examples of suitable substrates for gas fermentation include biogas and/or various components thereof, and syngas and/or various components thereof, each of which may be generated at any point in the biofuel production process or in a separate industrial process. For example, in one embodiment, the gas fermentation involves the production of ethanol from syngas. In one embodiment, the feed to the gas fermentation reactor includes biogenic carbon dioxide collected during the process. In one embodiment, the feed includes biogenic carbon monoxide collected during the process and/or generated from carbon dioxide that was collected during the process. In one embodiment, the gas fermentation involves the contact of the substrate gas in an aqueous fermentation medium with the fermentation microorganisms.

Advantageously, by using biogenic CO generated during the process and/or using biogenic carbon dioxide collected during the process as feed in a gas fermentation, wherein the process produces a fuel, a fuel intermediate, a chemical product or an energy product, a higher yield of biogenic carbon-based fuel may be produced, thus allowing a greater amount of the biogenic carbon from the feedstock to be converted to the final product. This in turn can result in significant improvements in biogenic product yield from the starting material. For example, in certain embodiments, the total energy of the biogenic carbon-based fuel or products that can be produced from the non-fossil organic material can be increased by at least 10%, 25% or 30% relative to a conventional biofuel production process without collecting carbon dioxide.

(a) Production Processes Using Hydrogen and Carbon Dioxide to Produce Carbon Monoxide The biogenic carbon dioxide and hydrogen sourced from fossil fuel may be used to produce carbon monoxide as a feedstock for the gas fermentation by the following reverse water gas shift reaction:

$$CO_2+H_2 \rightarrow CO+H_2O.$$

The carbon monoxide produced by the above reaction can be further converted in one or more chemical and/or biological steps to a fuel or fuel intermediate. For example, combining carbon monoxide from the above reaction with hydrogen results in syngas that can be used itself as a fuel or to produce a fuel or fuel intermediate. As described previously, examples of products made directly or indirectly from syngas include liquid hydrocarbons, methane, hydrogen, methanol, ethanol or ammonia.

The above reverse water gas shift reaction to produce carbon monoxide can be conducted as part of a reforming operation. According to such embodiment, the biogenic carbon dioxide and fossil derived hydrogen may be fed to a reformer. The steam reforming may be operated such that the foregoing reverse water gas shift occurs during the steam reforming, thereby producing carbon monoxide and water. The output from the steam reforming will then include syngas comprising carbon monoxide, hydrogen and carbon dioxide. The resultant syngas can subsequently be converted to products via one or more biologic and/or chemical conversions. In one embodiment, the syngas is converted to a hydrocarbon through a chemical conversion, such as the Fischer-Tropsch reaction described earlier or alternatively a process in which the syngas is converted to methanol and then to the hydrocarbon, such as gasoline, described in more detail hereinafter. In either case, the product from the syngas will contain biogenic carbon.

In one embodiment, the steam reformer is fed with a stream comprising biogenic carbon dioxide and methane derived from anaerobic digestion, along with fossil derived hydrogen. For example, in one embodiment the steam reformer is fed with a stream comprising biogenic carbon dioxide and methane from an anaerobic digestion of still bottoms. The presence of methane can aid in reducing the fossil hydrogen requirement because hydrogen is produced in situ from methane in the reformer.

In one embodiment, the fossil derived hydrogen is sourced from a process that produces fossil-containing molecules, such as carbon monoxide and/or carbon dioxide, and hydrogen from a fossil fuel hydrocarbon. In such process, the fossil-containing molecules are separated from the hydrogen. Preferably, all the carbon-containing molecules are removed, typically to achieve more than 90% or 95% by weight hydrogen. The hydrogen thus obtained is typically a low cost source compared to other sources, such as renewable sources. While hydrogen from fossil fuel may be used in the biofuel production, since the hydrogen does not itself contain fossil carbon the carbon dioxide tailpipe emissions that result from combustion of the biofuel, such as in transportation vehicles, contain only biogenic carbon, and thus are considered to have a neutral effect on atmospheric carbon dioxide levels. Although the carbon dioxide emissions associated with the hydrogen production from fossil fuels are included in the GHG emission analysis, in one embodiment, the life cycle GHG emissions of the fuel or fuels produced are reduced relative to a gasoline baseline using various approaches (e.g., placing the fossil-based $CO_2$ back underground), while at the same time advantageously using a low cost hydrogen source.

In one embodiment, the hydrogen is sourced from a third party. Sourcing the hydrogen includes directly or indirectly obtaining hydrogen for use in the production of the fuel or fuel intermediate, including obtaining the hydrogen from a third party. If the hydrogen is sourced from a third party, it may be obtained directly or indirectly by way of written documentation, including a contract, or other agreement between two or more parties.

The stream sourced from the hydrogen production process is referred to as a "stream enriched in hydrogen", meaning a stream comprising greater than 80 mol % hydrogen (mol:mol).

In one embodiment, the fossil derived hydrogen is produced by a process in which methane is converted to a syngas stream comprising carbon monoxide and hydrogen. Subsequently, further hydrogen enrichment steps may be conducted on the syngas stream or a stream derived therefrom to produce a stream with increased hydrogen content relative to syngas. The hydrogen may be enriched by various techniques known to those of skill in the art including by membranes, adsorbents or by further chemical conversions conducted to produce additional hydrogen.

In one embodiment, the hydrogen is sourced from reforming, such as steam methane reforming (SMR) or autothermal reforming (ATR). Both steam methane reforming and autothermal reforming methods operate by exposing the methane to a catalyst at high temperature and pressure to produce syngas, which is a mixture comprising hydrogen and carbon monoxide. Steam methane reforming is often referred to as a non-oxidative process that converts the methane into hydrogen and carbon monoxide by the following reaction:

$$CH_4+H_2O \rightarrow CO+3H_2.$$

Autothermal reforming uses oxygen and carbon dioxide or oxygen and steam in a reaction with methane to form carbon monoxide and hydrogen. The autothermal reaction using oxygen and carbon dioxide can be described by the following reaction:

$$2CH_4+O_2+CO_2 \rightarrow 3H_2+3CO+H_2O.$$

The autothermal reaction using oxygen and steam proceeds by the following reaction:

$$4CH_4+O_2+2H_2O \rightarrow 10H_2+4CO.$$

Examples of other reforming reactions include partial oxidation and dry reforming.

The hydrogen produced by the water gas shift reaction can be recovered from non-hydrogen components, including carbon dioxide, from a gaseous or liquid stream using known techniques employing adsorbents or membranes. An example of a recovery technique using adsorbents is pressure swing adsorption (PSA), which is commonly used to recover hydrogen produced by steam methane reforming. As would be appreciated by those of skill in the art, PSA is used to separate gas species from a mixture of gases under pressure using adsorbent materials such as zeolites, molecular sieves or activated carbon. The adsorbent material absorbs the target gas species at high pressure and the separation relies on the different affinity of various gas species in the gas stream. When the pressure is lowered, the target gas desorbs. In the practice of certain embodiments of the present invention, PSA adsorbs hydrogen and the desorption results in a stream concentrated in hydrogen. A stream comprising non-adsorbed species, including carbon dioxide, is also generated by PSA. This latter stream comprising carbon dioxide is often referred to as a purge gas stream.

As noted, carbon dioxide for introduction underground can be recovered from one or more streams comprising carbon dioxide generated during the above-mentioned hydrogen production process.

The reforming to produce syngas from biogenic carbon dioxide and hydrogen and the steam methane reforming and/or a water gas shift to produce hydrogen from fossil methane may generate excess heat. The heat generated from any one or a combination of these reforming and water gas shift operations may be used to provide energy in other unit operations. For example, the heat may be used to supply energy in a process to produce an energy product or a chemical product, a fuel or a fuel intermediate from the non-fossil organic material. The process can include the fermentation of non-fossil organic material to produce ethanol. For example, such heat can be utilized in a dryer, thermal oxidizer, distillation and/or evaporation in an ethanol production process using corn as a feedstock. Alternatively, the heat may be used in a production process to make ethanol from biomass or biomass derived material. This includes supplying heat to similar operations as a corn ethanol process or for pretreatment processes. In a further embodiment of the invention, heat from the reforming may be used to supply energy for a production process in which syngas is converted to a hydrocarbon through a chemical conversion such as that described above. In another embodiment, heat from the reforming is used to produce electricity either for internal use or for export to the grid. By implementing such energy savings, the life cycle GHG emissions can be reduced by at least 20% relative to a gasoline baseline. Advantageously, such GHG savings can enable the generation of a biofuel credit in relation to the fuel produced or sold.

The syngas produced by the reverse water gas shift may be converted to a fuel, fuel intermediate and/or chemical product via gas fermentation. In this embodiment, the CO in the syngas functions as a substrate for the biologic conversion, which utilizes microorganisms or other biocatalysts. For example, acetogenic microorganisms can be used to produce a biogenic carbon-based product from carbon monoxide through fermentation. For example, anaerobic microorganisms from the genus *Clostridium* can produce ethanol or other products from the carbon monoxide.

The production of ethanol by the acetogenic microorganisms proceeds through a series of biochemical reactions. Without being bound by any particular theory, the reactions carried out by the microorganism are as follows:

6CO+3H$_2$O→CH$_3$CH$_2$OH+4CO$_2$

6H$_2$+2CO$_2$→CH$_3$CH$_2$OH+3H$_2$O.

Some examples of strains that can produce ethanol from syngas are those from the genus *Clostridium*. In addition to ethanol, *Clostridium* bacteria may produce significant amounts of acetic acid (or acetate, depending on the pH) in addition to ethanol, although to improve ethanol yield it is possible to adjust fermentation conditions by nutrient limitation or by providing excess fossil derived hydrogen or carbon monoxide to achieve the desired ethanol productivity. Such conditions can be readily selected by those of skill in the art and it should be appreciated that the invention is not constrained by any particular set of parameters selected for fermentation to improve productivity.

Alternatively, the carbon monoxide from the above reverse water gas shift reaction can also be reacted with fossil derived hydrogen to produce methanol. The reactions are as follows:

CO$_2$+H$_2$→CO+H$_2$O (reverse water gas shift)

CO+2H$_2$→CH$_3$OH.

Alternatively, methanol is produced by the direct hydrogenation of CO$_2$ (not shown).

In one embodiment, the methanol is used as a fuel intermediate to make another fuel. Ethanol is one such fuel and its production from methanol can proceed by a variety of different reaction routes. The production of ethanol from methanol through organic acid intermediates, such as acetic acid, is known in the art. For example, methanol may be reacted with carbon monoxide to make acetic acid, acetate or a combination thereof, and the acetate is subsequently reacted with hydrogen to make ethanol and water. The reaction is as follows:

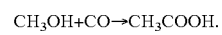

CH$_3$OH+CO→CH$_3$COOH.

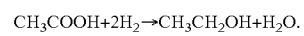

CH$_3$COOH+2H$_2$→CH$_3$CH$_2$OH+H$_2$O.

The hydrogenation of acetic acid may favour the production of ethyl acetate over ethanol. Special hydrogenating catalysts (e.g., platinum/copper or palladium/cobalt) may be used to produce ethyl acetate from acetic acid. The ethyl acetate may then be hydrogenated to ethanol. Ethanol production may also proceed via a methyl acetate intermediate. According to such embodiment, methanol is carbonylated to methyl acetate and optionally acetic acid. The methyl acetate is then hydrogenated to ethanol.

(b) Other Processes Employing Conversion of Biogenic CO$_2$ and Fossil Derived H$_2$ to Products Biogenic CO$_2$ and fossil derived H$_2$ may also be more directly converted to the biogenic carbon-based fuel or fuel intermediate rather than proceeding through a reverse water gas shift reaction to produce CO and H$_2$O. Representative examples of such processes are described below.

In one embodiment, the biogenic carbon dioxide and fossil derived hydrogen are subject to a gas fermentation. For example, according to one embodiment, the biogenic carbon dioxide and fossil derived hydrogen are converted to an alcohol, such as ethanol, by fermentation with a bacterium. In such embodiment, ethanol is produced from $CO_2$ and $H_2$ by the following reaction scheme:

$$6H_2 + 2CO_2 \rightarrow CH_3CH_2OH + 3H_2O.$$

The ethanol produced is referred to as "biogenic ethanol", meaning that carbon in the ethanol is from biogenic carbon or considered renewable or biogenic by those of skill in the art.

By adding fossil derived hydrogen, the above reaction can provide for significant yield increases relative to conventional ethanol production processes. In certain embodiments, the yield of ethanol achieved by the invention can be greater than 10%, 20% or 30% relative to the yield from conventional processes for producing biogenic ethanol from corn without collecting biogenic carbon dioxide and using it to make a product. Moreover, a byproduct generally considered a low energy waste product from processing of biomass or biomass-derived material may be converted into a valuable biofuel, in particular a biofuel that is eligible for fuel credit generation by virtue of its biogenic carbon. Further, using fossil derived hydrogen is uniquely low cost compared to other potential sources of hydrogen. Thus, in certain advantageous embodiments, a higher yield of biofuel may be achieved by a low cost method.

The production of ethanol from fossil derived hydrogen and biogenic carbon dioxide may be carried out with hydrogen oxidizing chemoautotrophs. In one embodiment, the microorganisms used include any bacteria from a genus selected from *Acetogenium, Acetobacterium, Acetoanaerobium, Butyribacterium* and *Clostridium* that are capable of the above bioconversion. In one embodiment, the microorganism used to produce ethanol is from the genus *Clostridium*. Without being limiting, a particularly suitable microorganism for producing ethanol from the biogenic carbon dioxide and fossil derived hydrogen is *Clostridium ljungdahlii*. This bacterium can effectively convert biogenic carbon dioxide and hydrogen to ethanol.

The fossil derived hydrogen is typically provided in excess of the biogenic carbon dioxide to satisfy the above stoichiometric molar ratio of $H_2:CO_2$ of 3:1 to produce ethanol. An example of a range of molar ratios of $H_2:CO_2$ that can be utilized is from 2:1 to 4:1 or from 2.5:1 to 3.5:1. The gases, hydrogen and carbon dioxide, are introduced to the fermentation unit, also referred to as a bioreactor, either together in a combined stream comprising both components or as separate respective streams. This includes the introduction of the gases together or separately along with broth. The bioreactor contains a liquid nutrient broth containing the bacteria and components required for their growth, such as vitamins and salts. In one embodiment, the bioreactor is one of a plurality of bioreactors in a system in which the reactors are arranged in series, parallel or a combination of such arrangements. In one embodiment the bioreactor includes a growth reactor may also be utilized which feeds a separate bioreactor in which most of the product ethanol is produced, or a growth phase may be carried out in a fermentation bioreactor itself.

The bioreactor for conducting the conversion may be a stirred or an unmixed tank reactor. An example of a bioreactor that can be used to ferment the fossil derived hydrogen and biogenic carbon dioxide is a deep tank bioreactor, which is a reactor generally having a depth of greater than 10 meters. The deep tank reactor may be stirred to facilitate contact between the gases and the liquid nutrient broth. The gases may also be introduced at the bottom region of the bioreactor and bubble through the liquid broth. Optionally, the gases are introduced along with the liquid broth, such as together with a broth re-circulation stream. Mechanical pumping may also be utilized to facilitate liquid flow and mass transfer. Another type of bioreactor that can be used is a gas lift reactor, wherein the broth is agitated through the use of gas nozzles.

The bioreactor may employ cell recycle in order to replenish the concentration of cells in the bioreactor. According to such embodiment, a liquid stream comprising cells is withdrawn from the reactor and sent to a solids-liquid separation (e.g., a microfiltration system or cell-retention system) to separate cells from the stream. The separated cells are returned to the bioreactor and a cell-free stream resulting from the separation may be sent to product recovery (e.g., for ethanol product recovery may include distillation). Product recovery and/or cell recycle may be continuous or intermittent.

Gases may accumulate in the headspace of the bioreactor. Such gases may be recycled back to the bioreactor or can be fed back to an SMR either as feedstock or as fuel. The gases withdrawn from the reactor may be combined with a stream comprising carbon dioxide and hydrogen introduced to the reactor.

While the production of ethanol from biogenic carbon dioxide and hydrogen has been described, hydrogen oxidizing chemoautotrophs can also produce acetic acid from these gaseous substrates. For example, *Clostridium* species are known to produce acetic acid by the following reaction mechanism:

$$4H_2 + 2CO_2 \rightarrow CH_3COOH + 2H_2O.$$

One fermentation parameter that may be selected to increase the production of acetic acid or ethanol is pH. For example, at pH values above about 5 *Clostridium* species may produce more acetic acid than ethanol, whereas at pH values above 3.8 and below about 5 *Clostridium* species may produce more ethanol. As would be appreciated by those of skill in the art, when the pH and/or other parameters are selected to produce acetic acid, acetic acid, acetate or both of these species will be present as dictated by the pH of the solution. The acetic acid may be sold as a product in either the acetate or acid form or converted to a fuel such as ethanol (e.g., via hydrogenation with fossil derived hydrogen).

Acetic acid and/or acetate can also be introduced back to an anaerobic digester and converted to methane by anaerobic digestion. The acetic acid and/or acetate introduced to an anaerobic digester can be a primary product of fermentation or a byproduct. Often fermentation of hydrogen and carbon dioxide to ethanol produces acetic acid and/or acetate as a byproduct. By recovering and introducing the acetic acid and/or acetate to anaerobic digestion, a byproduct from ethanol fermentation can be converted to biogas, thereby resulting in further potential improvements in the yield of fuel from the process.

According to one embodiment, the hydrogen production process to produce fossil derived hydrogen is conducted in close vicinity to a fermentation plant. An advantage of producing hydrogen close to a fermentation plant is that any energy generated during reforming can be used in various stages of a process to produce and recover a fermentation product. Since many stages of the fermentative process are energy-intensive, this can significantly reduce the costs of operating a fermentation plant. Energy savings from heat integration may also contribute to reducing the life cycle GHG emissions of a fuel relative to a gasoline baseline and thus can potentially enable the generation of a valuable biofuel credit in relation to the fuel produced or sold.

For instance, the heat from reforming carried out during the hydrogen production can be used to supply energy for processes comprising a fermentation from which the biogenic $CO_2$ feed is collected and used to produce the biogenic carbon-based fuel, fuel intermediate or chemical product. For example, such heat can be utilized in a dryer, thermal oxidizer, distillation and/or evaporation conducted as part of a process comprising fermentation. Such steps are often part of a production process comprising fermentation using corn as a feedstock, although the heat from reforming can be used in any production process comprising fermentation to make a fermentation product, including processes using biomass or biomass derived material. In those processes using corn as a feedstock, driers used to dry still bottoms remaining after distillation of ethanol to produce products such as dried distiller's grains are especially energy-intensive to operate and so using a portion of the heat from reforming at this stage of a production process can potentially make the process significantly more efficient.

Alternatively, or in addition, the heat generated from reforming may be used to provide energy in other unit operations besides production processes comprising fermentation. For instance, heat from the reforming can also be used to supply energy for processes in which syngas is converted to a fuel or fuel intermediate.

Combination of Two Fermentations

As discussed above, fuels and/or fuel intermediates containing biogenic carbon may be produced via gas fermentation of a feedstock that includes at least one of CO and $H_2$. For example, biogenic carbon dioxide and hydrogen sourced from fossil fuel may be used to produce carbon monoxide (e.g., which is used as a feedstock for the gas fermentation) by the following reverse water gas shift reaction:

$$CO_2 + H_2 \rightarrow CO + H_2O.$$

The carbon monoxide produced by the above reaction can be further converted in one or more chemical and/or biological steps to the biofuel or biofuel intermediate. In particular, syngas from the reverse water gas shift may be converted to ethanol and/or acetic acid via a biologic conversion utilizing microorganisms or other biocatalysts. For example, acetogenic microorganisms, such as anaerobic microorganisms from the genus *Clostridium*, may produce ethanol from carbon monoxide. Without being bound by any particular theory, the reactions carried out by the microorganism may be as follows:

$$6CO + 3H_2O \rightarrow CH_3CH_2OH + 4CO_2$$

$$6H_2 + 2CO_2 \rightarrow CH_3CH_2OH + 3H_2O.$$

As discussed above, the CO may be obtained from the hydrogenation of biogenic carbon dioxide, and/or may be obtained from another part of the process. For example, in one embodiment, the CO and $H_2$ is sourced from syngas, which is produced from gasification of cellulosic feedstock according to the following reaction:

$$8CH_2O + O_2 \rightarrow 6CO + 2CO_2 + 8H_2.$$

For example, syngas may be obtained from the gasification of biomass, cellulosic feedstock and/or lignin. The syngas may be collected and is optionally combined with bio-$CO_2$ collected from other parts of the process (e.g., fermentation, anaerobic digestion, etc.), and feedstock and/or lignin. Some examples of products (e.g., including fuels and fuel intermediates) made directly or indirectly from the gas fermentation of syngas include ethanol, butanol, acetic acid, and/or butyric acid. In general, the product will depend, at least in part, on the microorganism and the fermentation conditions.

Unfortunately, the fermentation products produced by gas fermentation are often relatively dilute (e.g., the concentration of ethanol produced by a typical gas fermentation is may be between about 15 and about 35 g/L for a continuous fermentation, whereas the concentration of ethanol in a typical corn fermentation may be between about 95 and 140 g/L, and for a biomass fermentation may be between about 50 and 100 g/L). As a result of the low concentration, process for recovering the fermentation product may require a large amount of energy (e.g., heat for the distillation, etc.), which also results in increased GHG emissions and increased costs. For example, the product recovery costs in a stand-alone gas fermentation can be a significant portion of the overall capital and operating costs.

In accordance with one embodiment of the instant invention, at least a portion of the relatively dilute fermentation product (e.g., ethanol, acetic acid, etc.) produced during gas fermentation is introduced to and/or used in the carbohydrate fermentation. Carbohydrate fermentation processes often require an amount of water be added to the substrate to enable an aqueous fermentation. Traditionally, this water may be recycled from the process. For example, in producing ethanol, the recycled water may originate from the still bottoms. For example, the still bottoms may be subject to a solid/liquid separation and/or a water removal step such as evaporation or reverse osmosis, and recycle streams may be obtained from still bottoms, filtered still bottoms or from the water removal step. However, in accordance with one embodiment of the instant invention, an aqueous stream comprising the gas fermentation product is introduced into the carbohydrate fermentation unit to provide at least a portion of the water required to enable such fermentation.

In accordance with one embodiment of the instant invention, at least a portion of the relatively dilute gas fermentation product is added to the process at a step upstream of the carbohydrate fermentation. Carbohydrate fermentations may require an amount of water be during one or more processing steps (e.g., added for grinding, liquefaction, and/or separation). For example, a conventional carbohydrate fermentation process may require that water be added to dry-milled corn meal to provide a slurry, be added during pretreatment/hydrolysis of a cellulosic feedstock, or be added during the saccharification of starchy feedstock, etc. In one embodiment, the gas fermentation product stream is added to any processing step within the carbohydrate fermentation process wherein it is required that water be added.

In one embodiment, at least a portion of the aqueous stream comprising the gas fermentation product is added anywhere in the process such that at least a portion of the gas fermentation product enters the carbohydrate fermentation unit, and such that the concentration of fermentation product exiting the carbohydrate fermentation unit is greater than the concentration of fermentation product in the aqueous stream exiting the gas fermentation unit.

In one embodiment, at least a portion of the aqueous stream comprising the gas fermentation product is added between, before, or after the processing steps or at stages ancillary to the main processing steps.

Advantageously, adding the dilute gas fermentation product to a stage in the process that requires water, reduces the amount of water that needs to be imported into the process and/or recycled from another part of the process. Furthermore, since the water generated in and/or required for the gas fermentation is used within the process, there are significant energy reductions (e.g., and thus GHG and cost reductions) related to not having to separate the gas fermentation product from the water used in the gas fermentation. In other words, since the water containing the dilute product from the gas fermentation replaces water that would otherwise have been added to a step in the process, the cost corresponding to recovering the fermentation product from the dilute stream can be substantially reduced.

Moreover, when the gas fermentation product and the carbohydrate fermentation product correspond to the same fermentation product (e.g., ethanol, acetic acid, etc.), the gas fermentation product may be carried through the various steps of the carbohydrate fermentation process and combined with the carbohydrate fermentation product to improve overall cost of production. The phrase "same product" or "same fermentation product", as used herein, refers to products having the same chemical formula. Accordingly, ethanol produced from a carbohydrate fermentation (i.e., bioethanol) is considered to be the same product as ethanol containing fossil carbon.

As discussed above, introducing an aqueous stream comprising the gas fermentation product into the process such that the concentration of total fermentation product (e.g., provided by gas and carbohydrate fermentations) increases at the output of the carbohydrate fermentation per unit carbohydrate consumed, a can reduce overall costs. In one embodiment, the concentration of the fermentation product at the output of the carbohydrate fermentation unit is at least about 3% (w/w) higher than the concentration of the gas fermentation product at the output of the gas fermentation unit. In one embodiment the concentration of the fermentation product at the output of the carbohydrate fermentation unit is at least about 25 g/L higher than the concentration of the gas fermentation product at the output of the gas fermentation unit. In other embodiments, the concentration of the fermentation product at the output of the carbohydrate fermentation unit is about 50 g/L or 70 g/L higher.

In one embodiment, wherein the concentration of fermentation product produced in the carbohydrate fermentation is limited by fermentation conditions, adding the aqueous stream containing the gas fermentation product may result in the carbohydrate fermentation requiring less feedstock to produce the same concentration of fermentation product.

In accordance with one embodiment, the gas fermentation produces biogenic ethanol, thus improving the overall yield of biogenic ethanol from a given amount of carbohydrate. The production of ethanol via bio-CO and/or bio-$CO_2$ fermentation advantageously converts low cost gas streams into valuable liquid biofuel. Moreover, it increases the total yield of bioethanol from a cellulosic ethanol plant, using waste streams (e.g., $CO_2$) that otherwise would be vented. Unfortunately, gas fermentation does not typically produce fermentation products, such as ethanol, at high concentrations, as discussed above, and thus traditionally has been associated with higher product recovery costs.

In accordance with one embodiment, gas fermentation and conventional carbohydrate fermentation are integrated within the same process such that the total cost (e.g., capital and operating) of the gas fermentation and carbohydrate fermentation is lower than if the two product recoveries were performed independently. For example, a stand-alone gas fermentation process would require significant ancillary systems and/or high energy input, and thus would have relatively high overall capital costs. However, when used within a cellulosic ethanol plant, the ethanol produced in the gas fermentation (e.g., having a relatively low concentration) would be additional to the ethanol formed in the carbohydrate fermentation (e.g., having a relatively high concentration), thus increasing the fermentation product concentration and thus lowering the overall capital and operating costs of product recovery.

In one embodiment, the substrate for the gas fermentation includes at least CO, and thus may be obtained from waste streams of various industries (e.g., steel mill). In one embodiment, the substrate for the gas fermentation contains only syngas, which as described in greater detail below may be generated from one or more thermal processes in the process, and/or may be derived from biogas generated during the process. In one embodiment, the substrate for the gas fermentation includes syngas and/or a stream of carbon dioxide, which as described in greater detail below may be generated and/or collected from the process (e.g., in a thermal process).

In one embodiment, the gas fermentation and carbohydrate fermentation are part of different processes and/or provided by different parties. For example, in one embodiment, the gas fermentation is conducted by an industrial plant that uses a CO containing waste gas stream (e.g., fossil based) as the substrate for the gas fermentation, whereas the carbohydrate fermentation is conducted by an ethanol producer (e.g., corn, sugar cane, or cellulosic). In one embodiment, the industrial plant, which may be in close proximity to the ethanol producer, exports the aqueous stream containing the gas fermentation product to the ethanol producer, while the ethanol producer exports biogenic carbon dioxide to be used in the gas fermentation.

While the gas fermentation may be conducted only with the CO-rich stream, introducing additional $CO_2$ may increase the yield of fermentation product (e.g., based on stoichiometry). Moreover, importing biogenic $CO_2$ may increase the amount of biogenic ethanol that could be recovered from the ethanol producers.

Thermal Processes

In one embodiment, one or more thermal processes are carried out to produce a fuel, fuel intermediate, chemical product and/or an energy product. Some examples of thermal processes include combustion, gasification, pyrolysis, or a combination thereof. Some examples of materials to be fed to the thermal process includes solids from a pretreated cellulosic feedstock (e.g., wherein the solids are provided by a solid/liquid separation performed after washing the pretreated feedstock), solids provided by a solid/liquid separation performed after hydrolysis and/or fermentation, and solids provided by a solid/liquid separation of still bottoms.

In one embodiment, an energy product is produced by combustion of the non-fossil organic material. In one embodiment, a fuel, fuel intermediate, or chemical product is produced by gasification or pyrolysis. Some examples of fuels, fuel intermediates or chemical products produced from the gasification or pyrolysis of non-fossil organic material include syngas, hydrogen, methane, liquid hydrocarbons, pyrolysis oil, and ammonia. Some examples of combustion, gasification and pyrolysis, and products generated from these processes, are described in more detail below.

In general, combustion may include one or more exothermic reactions between the non-fossil organic material and an oxidant, which is typically air or oxygen. Combustion of the non-fossil organic material may be conducted in a power plant. In such embodiments, carbon dioxide is recovered from a gas stream, known in the art as "flue gas".

The combustion may be carried out with a gas having an oxygen content exceeding that of air, known in the art as an "oxyfuel combustion process". In one embodiment, the flue gas may be re-circulated to the combustion and mixed with an oxygen stream as part of the oxyfuel combustion process. An advantage of oxyfuel combustion processes is that combusting in the presence of oxygen removes contaminants. The result is a flue gas having a high concentration of carbon dioxide, which may be collected with relative ease.

The non-fossil organic material may be fed to a combustion apparatus, such as a steam boiler and the heat generated utilized to produce electricity, steam, process heat, building heat, or any combination of thereof. The boiler generally includes a section in which water or other fluid is heated. The heat produced from the burning of organic material may be transferred to boiler feed water to produce steam. The boiler may be a fluidized bed boiler, although other types of boilers may be used as required. The feed to the boiler may also include biogas produced during anaerobic digestion. Moreover, during the start-up stage of the process, a small amount of natural gas may be added to the boiler to heat the fuel to the ignition point. Depending on the emissions regulations, exhaust from the boiler may be passed to a scrubber or other series of operations to reduce pollutant levels before being discharged to the environment. As well, particulate matter may be removed from the exhaust. Ash from the boiler may be landfilled or sold as a co-product depending on its composition.

The steam may be used to drive turbines to create electricity for sale to the power grid and/or to meet plant needs. Alternatively, or in addition to electricity generation, the steam can be used to supply process heat needs within a plant. If the steam is used within a plant, the pressure may be reduced prior to its re-use in the process. Furthermore, the steam can be utilized to provide building heating. One example of an organic material often subjected to combustion is lignin.

While combustion often produces an energy product, gasification is often carried out to produce syngas. Gasification includes heating at elevated temperature, generally in the presence of oxygen. Gasification of biomass or biomass derived products can be carried out according to the following reaction:

$$8CH_2O+O_2 \rightarrow 6CO+2CO_2+8H_2.$$

The carbon dioxide produced by the above reaction can be collected as set out below. The syngas can, in turn, be used as an intermediate to produce another fuel or fuel intermediate, as set forth previously, or used as a fuel itself. In one embodiment, the biogenic carbon dioxide for the gas fermentation is sourced from syngas. For example, in one embodiment, biogenic carbon dioxide can be collected from one or more stages of a gasification process or downstream stages, such as product synthesis processes, and purified. The purified biogenic carbon dioxide may then be converted to a biogenic carbon-based fuel or fuel intermediate via the gas fermentation. In another embodiment, the biogenic carbon dioxide is collected from a waste gas stream that remains after combustion of a gas stream containing both combustible gases and carbon dioxide. Burning of the combustible gases in the mixture forms carbon dioxide and the resulting stream enriched in carbon dioxide can subsequently be used to make a biogenic carbon-based fuel or fuel intermediate. In another embodiment, the biogenic carbon dioxide is sourced from biogas. In another embodiment, the biogenic carbon dioxide is sourced from gases generated during carbohydrate fermentation. In another embodiment, the biogenic carbon dioxide is generated during a process that includes subjecting syngas to a water gas shift reaction, as follows:

$$CO+H_2O \rightarrow CO_2+H_2.$$

In another embodiment, one or more of the above-mentioned sources of $CO_2$ are combined and then subject to a gas fermentation to produce a fuel or fuel intermediate (e.g., such as alcohol).

Like gasification, pyrolysis often produces syngas. For example, pyrolysis typically includes heating non-fossil organic material at elevated temperature to produce syngas, char and/or pyrolysis oil and may be carried out in the absence of oxygen or at low levels thereof. Carbon dioxide may be collected from a stream resulting from a water gas shift reaction carried out on the syngas or other streams generated during the process that contain carbon dioxide. Pyrolysis oil, also referred to as bio-oil, is produced by subjecting the non-fossil organic material to pyrolysis at elevated temperature, typically lower than gasification. Pyrolysis oil can be treated further to produce a transportation fuel such as diesel or used directly as a fuel.

Collecting Biogenic Carbon Dioxide

As mentioned above, biogenic carbon dioxide may be generated (e.g., directly or indirectly) during fermentation, anaerobic digestion, and/or a thermal process. Those skilled in the art will appreciate that the biogenic carbon dioxide can be sourced directly from a production process using non-fossil organic material as a feedstock or it can be fossil carbon dioxide, or a mixture of fossil and non-fossil carbon dioxide that is sourced more indirectly from such organic material. Thus, "biogenic carbon dioxide" as used herein includes carbon dioxide that is (a) obtained from a production process using non-fossil organic material as a feedstock; (b) withdrawn from an apparatus for transporting carbon dioxide, which withdrawn carbon dioxide is from fossil sources or contains a mixture of carbon dioxide from fossil and non-fossil sources and that is considered renewable due to the introduction of an amount of carbon dioxide produced by such production process to the apparatus that corresponds to the amount of carbon dioxide withdrawn; or both (a) and (b).

In one embodiment, the biogenic carbon dioxide is "collected", by which it is meant any suitable process for obtaining carbon dioxide during or after its generation, and may include single or multi-stage processes. The biogenic carbon dioxide may be collected along with other non-$CO_2$ components. That is, collection of carbon dioxide may comprise obtaining a stream comprising biogenic carbon dioxide and optionally one or more non-$CO_2$ components. To illustrate, collecting a crude biogas stream, from a landfill or a digester, comprising carbon dioxide along with other components such as methane and hydrogen resulting from anaerobic digestion constitutes collection of biogenic carbon dioxide. To further illustrate, collecting carbon dioxide may comprise obtaining a stream comprising carbon dioxide enriched by recycle.

The biogenic carbon dioxide may be enriched by purification, recycle or the like. The purification may, for instance, include a process in which carbon dioxide is separated from other constituents in a stream or other processes that produce a stream enriched in carbon dioxide. Such other processes include combusting a carbon dioxide-containing stream comprising combustible carbon to produce a stream comprising additional carbon dioxide resulting from the combustion. Recycling of a stream comprising carbon dioxide may result in enrichment of carbon dioxide as well due to the increase in concentration of carbon dioxide during re-circulation. A stream enriched in biogenic carbon dioxide may also be a waste stream generated during the process. The $CO_2$-enriched stream may comprise at least 60%, at least 70%, at least 80%, or at least 90% carbon dioxide by weight.

In certain non-limiting embodiments, the level of carbon dioxide recovery from a gaseous or liquefied mixture may be at least 40% by weight, at least 50% by weight, at least 60% by weight, at least 70% by weight, at least 80% by weight, at least 90% by weight or at least 95% by weight.

Non-limiting examples of known collection methods include separating biogenic carbon dioxide from a gaseous mixture with a liquid absorbent or solid sorbent, membrane separation or separation of carbon dioxide from other constituents in liquid form. Carbon dioxide can be separated from impurities in a gas stream using a liquid absorbent, such as a solvent or solid sorbent that is capable of capturing carbon dioxide. After capturing carbon dioxide, the liquid absorbent or solid sorbent is regenerated to release the carbon dioxide. The liquid absorbent or solid sorbent can subsequently be used to capture more carbon dioxide. A solid sorbent includes minerals, zeolites and activated carbon. Membranes are materials that allow the selective permeation of a gas through them. Membrane materials may be polymeric, metallic or ceramic and the selectivity of the membrane for the gaseous constituents depends on nature of the material of which it is made.

Separation of carbon dioxide from other constituents in liquid form may involve liquefying a gas comprising carbon dioxide by compression, cooling and expansion steps. When in liquid form, the carbon dioxide can be separated by distillation. Refrigerated systems may also be used for carbon dioxide separation.

A number of specific techniques for obtaining carbon dioxide from various gaseous streams resulting from fermentation, gasification, pyrolysis or combustion are described below. However, it will be understood by those having ordinary skill in the art that other methods of recovering biogenic carbon dioxide, as would be known to those skilled in the art, are also possible.

Known techniques for collecting carbon dioxide from fermentations include the use of liquid absorbents. For example carbon dioxide can be recovered using a scrubbing unit in which water is flowed counter-current to the carbon dioxide-containing stream to remove water and water soluble components, including the fermentation product. Water that remains in the carbon dioxide is subsequently removed in a compressor to increase the pressure of the carbon dioxide up to the water condensation level. The carbon dioxide may be fed to a drying unit to remove additional water. A purifying unit, which typically contains activated carbon, may be included in the process configuration before or after the drying unit to remove impurities. Inert gases, such as nitrogen (also referred to in the art as non-condensable or permanent gases), may subsequently be removed in a condenser.

Carbon dioxide can be recovered from crude syngas produced from gasification or from a stream resulting from reacting the carbon monoxide with steam in a water gas shift reaction to produce a stream comprising carbon dioxide and hydrogen. Further, the biogenic carbon dioxide may be collected from excess carbon dioxide generated during the gasification or collected from a recycle stream, such as, without limitation, a carbon dioxide stream recycled during syngas fermentation.

Without being limiting, the carbon dioxide can be separated by physical or chemical absorption to produce a carbon dioxide-containing stream. The physical absorption may involve the use of membranes that allow the selective permeation of a gas through them. For example, the carbon dioxide can be recovered by membranes that are more permeable to carbon dioxide than other components in the carbon dioxide-containing stream. The carbon dioxide passes through the membrane while other components do not, thereby resulting in a stream that is carbon dioxide enriched. The carbon dioxide-enriched stream can be used in gas or liquid form. Chemical absorption involves the use of chemical solvents. Examples of chemical solvents include methanol, N-methyl 2 pyrrolidone, dimethyl ethers of polyethylene glycol, potassium carbonate, monoethanolamine, methyldiethylamine and tetrahydrothiophene 1,1-dioxide. A known method for recovering carbon dioxide from a stream comprising carbon dioxide and hydrogen resulting from a water gas shift reaction is a Rectisol® wash process that uses methanol as a solvent. Amine gas scrubbing is another example of a technique involving chemical absorption. A prevalent amine for such applications in monoethanolamine.

Carbon dioxide can be obtained from a gaseous stream, such as a flue gas stream produced from a combustion process that uses the non-fossil organic material as a feed. This includes combustion of organic material in a power plant, such as a plant that otherwise burns fossil fuel such as natural gas or coal. Such a combustion includes an oxyfuel combustion process.

Gaseous streams from combustion contain carbon dioxide and other impurities depending on the source. Carbon dioxide can be separated from impurities in the gas stream using a liquid absorbent or solid sorbent that is capable of capturing carbon dioxide. The liquid absorbent may be a chemical solvent, such as an amine, or a Selexol™ solvent which uses polyethylene glycol as a solvent. The liquid absorbent can be added as part of a scrubbing operation, such as amine scrubbing. Regeneration of the chemical solvent may then be conducted by stripping or other separation techniques, with the regenerated chemical solvent being used to capture more carbon dioxide. A solid sorbent may include a zeolite or activated carbon. For solid sorbents, regeneration may be achieved by a change in pressure or temperature, thereby releasing the carbon dioxide and regenerating the sorbent for further use.

Biogenic carbon dioxide from oxyfuel combustion can be separated from other gaseous components by distillation. A carbon dioxide-containing stream can be liquefied by compression, cooling and expansion steps. The carbon dioxide can subsequently be separated in liquid form in a distillation column. A further example of a technique for carbon dioxide separation from other components is refrigerated separation. Distillation or refrigerated separation can also be used to separate carbon dioxide from synthesis gas that has undergone a water-gas shift conversion of carbon monoxide to carbon dioxide.

The biogenic carbon dioxide may be collected from two or more separate steps of a process to convert the organic material to a fuel, fuel intermediate or energy product. To illustrate, carbon dioxide may be collected from a fermentation of organic material to produce a liquid fuel, such as an alcohol. In addition, carbon dioxide may be recovered from an anaerobic digestion or gasification of a waste stream generated from such liquid fuel fermentation. By collecting carbon dioxide from two or more steps of the same or different processes, the yield of the fuel, fuel intermediate, chemical product or energy product from the organic material can be further increased.

Reducing GHG Emissions

In on embodiment, the process includes carrying out or arranging for one or more parties to carry out at least one step that contributes to a reduction in the life cycle GHG emissions of one or more biogenic carbon-based fuels produced directly or indirectly by the process. In certain embodiments, the life cycle GHG emissions can be at least 20%, 30%, 40%, 50%, 60%, 70% or 80% less than a gasoline baseline. Such reductions in life cycle GHG emissions can allow for advantaged fuel credit generation, as discussed below.

As used herein "arranging" or "causing" means to bring about, either directly or indirectly, or to play a required role in a series of activities through commercial arrangements such as a written agreement, verbal agreement or contract.

In one embodiment, GHG emissions are reduced by introducing fossil carbon dioxide, which is generated during the production of hydrogen from fossil fuel hydrocarbon, underground. For example, the fossil carbon dioxide may be introduced into an underground geological formation, thereby reducing life cycle GHG emissions by preventing carbon from fossil sources from being emitted to the atmosphere. Without being limiting, the fossil carbon dioxide may be introduced underground for extracting oil or gas in an enhanced oil or gas recovery. A description of enhanced oil and gas recovery is set forth in U.S. Patent Publication No. 2013/0089905 (published Apr. 11, 2013), which is incorporated herein by reference and particularly for the purpose of describing enhanced oil and gas recovery. The enhanced oil or gas recovery is any process that enables the recovery of underground oil or gas with the aid of fluid, including liquid or gas injection or two-phase fluid, such as foam. Carbon dioxide can also be injected into saline aquifers or other geologic formations in which the carbon dioxide can be contained, although as would be appreciated by those of skill in the art, some amount of carbon dioxide leakage may occur from the formation over a relatively long period of time. In another embodiment, the reducing GHG emissions are reduced by incorporating the fossil carbon dioxide into manufactured chemical products such as sodium bicarbonate and/or calcium carbonate that are stable and thus greatly slow or substantially prevents the fossil carbon dioxide from being emitted into the atmosphere.

In order to transport the fossil carbon dioxide to the proximity of an underground geologic formation, it may be introduced to an apparatus for transporting carbon dioxide, such as a pipeline, railroad car or truck. An amount of carbon dioxide is withdrawn from the transport apparatus for introduction underground, typically by a different party than the party that generates the carbon dioxide. In this case, the party that produces the fossil derived hydrogen and the fossil carbon dioxide may arrange for, or cause, a third party to withdraw an amount generally corresponding to that introduced to the transport apparatus (e.g., pipeline).

According to one embodiment, a chemical or energy product produced or derived from the non-fossil organic material may displace a chemical or energy product made from fossil fuel. By displace, it is meant that the energy product or chemical product, reduces or is recognized by those skilled in the art as reducing, the production and/or use of a corresponding fossil derived energy or chemical product, thereby reducing the life cycle GHG emissions associated with the biofuel. The GHG emission reductions are typically reflected in a life cycle GHG emission calculation. The GHG emissions for production or use of the chemical or energy product are thereby reduced because the GHG emissions associated with the displaced chemical or energy product from fossil fuel are avoided, and replaced with a chemical or energy product produced or derived from non-fossil organic material. The chemical or energy product produced from fossil fuel energy sources is referred to as a fossil derived chemical or energy product.

Fossil derived hydrogen can also be transferred by a transport apparatus, such as a pipeline, railroad car or truck. In some embodiments, collection of carbon dioxide from the hydrogen production process reduces the GHG emissions attributable to hydrogen and such beneficial environmental attributes may be transferred by feeding such hydrogen into a transport apparatus and withdrawing an equivalent amount from the transport apparatus, thus transferring the environmental attributes to the withdrawn hydrogen.

By way of example, the electricity produced by combusting biomass or biomass derived material, such as lignin, may displace the production or use of fossil derived electricity from a coal burning power plant. Displacement of an energy product generally involves exporting the energy product from the process. However, it will be appreciated that displacement encompasses the use of an energy product as an energy source for a stage within the process itself. For example, electricity and/or heat produced by combusting lignin can be used to provide energy for the production process that produces a product derived from the non-fossil organic material. According to one embodiment, lignin that results after a production process in which a lignocellulosic feedstock is converted to sugar, and fermented to produce a fermentation product, is burned to generate electricity and/or heat, which is subsequently used in one or more stages within the production process to supply energy in the form of heat and/or electricity. As would be appreciated by those of skill in the art, such embodiment can displace the use of fossil fuel since there is a reduction of the production or use of fossil derived energy. In one embodiment, an energy product is both exported and also used within the process itself as an energy source.

In a further example, a chemical product such as acetic acid derived from non-fossil organic material can displace acetic acid made from fossil sources. Similarly, a chemical product produced by the process could be used within the process itself to reduce chemical usage, thereby reducing the use or production of a corresponding product made from fossil sources.

While the production of a fermentation product, such as ethanol, has been described with regard to using a gas feed containing biogenic carbon, it is also possible for the gas feed to include fossil carbon (e.g., obtained from steam methane reforming).

Determining Life Cycle GHG Emissions

According to one embodiment, one or more biogenic carbon-based fuel(s) produced as a result of the process has life cycle GHG emissions associated therewith that are at least 20%, 30% or 40% lower than a gasoline baseline. In one embodiment, the savings can be at least as much as 50% lower than a gasoline baseline, or even at least as much as 60%, 70%, 80% or 90% lower than a gasoline baseline.

To determine life cycle GHG emissions associated with a biogenic carbon-based fuel, analyses are conducted to calculate the GHG emissions related to the production and use of the fuel throughout its life cycle. Life cycle GHG emissions include the aggregate quantity of GHG emissions related to the full life cycle of the transportation or heating fuel, including all stages of fuel and feedstock production and distribution, from feedstock generation or extraction through the distribution and delivery and use of the finished fuel to the ultimate consumer. GHG emissions account for total net GHG emissions, both direct and indirect, associated with feedstock production and distribution, the fuel production and distribution and use.

Examples of Methodologies for Calculating Life Cycle GHG Emissions

Because many of the laws adopted differentiate the requirements for fuels based upon their net GHG emissions impacts, those skilled in the art are familiar with methods to analyze and characterize the expected net GHG emissions of fuel pathways that regulators have developed and/or adopted. Thus, life cycle GHG emissions are determined in accordance with such methods known to those skilled in the art, in accordance with prevailing rules and regulations.

Life cycle GHG emissions evaluations generally consider GHG emissions associated with each of:
(a) feedstock production and recovery, including the source of carbon in the feedstock, direct impacts such as chemical inputs, energy inputs, and emissions from the collection and recovery operations, and indirect impacts such as the impact of land use changes from incremental feedstock production;
(b) feedstock transport, including feedstock production and recovery and GHG emissions from feedstock transport including energy inputs and emissions from transport;
(c) fuel production, including chemical and energy inputs, emissions and byproducts from fuel production (including direct and indirect impacts); and
(d) transport and storage of the fuel prior to use as a transportation or heating fuel, including chemical and energy inputs and emissions from transport and storage.

Known models to measure life cycle GHG emissions associated with the one or more fuels of the invention, include, but are not limited to:
(i) GREET Model—GHGs, Regulated Emissions, and Energy Use in Transportation, the spread-sheet analysis tool developed by Argonne National Laboratories;
(ii) FASOM Model—a partial equilibrium economic model of the U.S. forest and agricultural sectors developed by Texas A&M University;
(iii) FAPRI International Model—a worldwide agricultural sector economic model that was run by the Center for Agricultural and Rural Development ("CARD") at Iowa State University;
(iv) GTAP Model—the Global Trade Analysis Project model, a multi-region, multi-sector computable general equilibrium model that estimates changes in world agricultural production as well as multiple additional models; and
(v) ISO (International Organization for Standardization) standards for GHG emissions accounting and verification—provides guidance for quantification, monitoring and reporting of activities intended to cause greenhouse gas (GHG) emission reductions or removal enhancements.

The life cycle GHG emissions or carbon intensity of the biogenic carbon-based fuel is generally measured in carbon dioxide equivalents ($CO_2eq$). As would be understood by those of skill in the art, carbon dioxide equivalents are used to compare the emissions from various GHGs based upon their global warming potential (GWP), which is a conversion factor that varies depending on the gas. The carbon dioxide equivalent for a gas is derived by multiplying the amount of the gas by the associated GWP.

$$\text{grams of } CO_2eq = ((\text{grams of a gas})*(\text{GWP of the gas})).$$

The GWP conversion value used to determine grams of $CO_2eq$ will depend on applicable regulations for calculating life cycle GHG emissions reductions. The GWP under EISA is 1, 21 and 310, respectively, for carbon dioxide, methane and nitrous oxide as set forth in Renewable Fuel Standard Program (RFS2) Regulatory Impact Analysis, February 2010, United States Environmental Protection Agency, EPA-420-R-10-006, pg. 13, of which the entire contents are incorporated herein by reference. Under California's LCFS, the GWP is 1, 25 and 298, respectively, for carbon dioxide, methane and nitrous oxide, as measured by the GREET model. It should be appreciated that GWP values can be readily calculated by those of skill in the art in accordance with regulations.

The unit of measure for carbon intensity or life cycle GHG emissions that may be used to quantify GHG emissions of the biogenic carbon-based fuel is grams $CO_2eq$ per MJ of energy in the fuel or grams $CO_2eq$ per million British thermal units of energy in the fuel (MMBTU). The units used to measure life cycle GHG emissions will generally depend on applicable regulations. For example, under the EPA regulations, GHG emissions are measured in units of grams $CO_2eq$ per million BTUs (MMBTU) of energy in the fuel. Under LCFS, GHG emissions are measured in units of grams $CO_2eq$ per MJ of energy in the fuel and are referred to as carbon intensity or CI.

In general, the life cycle GHG emissions of the biogenic carbon-based fuel are compared to the life cycle GHG emissions for gasoline, referred to as a gasoline baseline. GHG life cycle emissions are compared by reference to the use of gasoline per unit of fuel energy.

The EPA value for the gasoline baseline used in life cycle GHG emission calculations is 98,204 g $CO_2eq$/MMBTU or 93.10 g $CO_2eq$/MJ. Under California's LCFS, the gasoline baseline is 95.86 g $CO_2eq$/MJ. Those of ordinary skill in the art can readily convert values herein from g $CO_2eq$/MJ to g $CO_2eq$/MMBTU or g $CO_2eq$/MMBTU to g $CO_2eq$/MJ by using an appropriate conversion factor.

The life cycle GHG emission reduction relative to a gasoline baseline is calculated using "EPA methodology", which means determining life cycle GHG emissions reductions by known methods as disclosed in EPA-420-R-10-006, "Renewable Fuel Standard Program (RFS2) Regulatory Impact Analysis", February 2010, which is incorporated herein by reference. In addition, for situations in which fossil carbon dioxide is introduced underground, such determination of life cycle GHG emission reduction includes a GHG saving that corresponds to the amount of carbon dioxide introduced underground. For example, one tonne of fossil carbon dioxide introduced underground would be counted as one tonne GHG savings in a life cycle GHG emission calculation. As would be appreciated by those of skill in the art, this method has been used by the EPA to quantify GHG savings due to the introduction of CO2 underground that is captured from power plants. (See EPA-HQ-OAR-2013-0495, Jan. 8, 2014).

In one embodiment, the life cycle GHG emission reduction relative to a gasoline baseline is measured using "LCFS methodology", which means measuring life cycle GHG emissions reductions by California's LCFS methodology using the GREET model, as set forth in Detailed California-Modified GREET Pathway for Corn Ethanol, California Environmental Protection Agency, Air Resources Board, Jan. 20, 2009, Version 2.0.

In one embodiment, the life cycle carbon dioxide emissions, rather than the life cycle GHG emissions, are determined for the biogenic carbon-based fuel and compared to a gasoline baseline. For example, as would be appreciated by those of skill in the art, when a reduction in carbon dioxide emissions relative to a production process baseline is quantified, a life cycle carbon dioxide emission reduction can be quantified instead of a life cycle GHG emission reduction.

Meeting Renewable and Low Carbon Fuel Targets

Advantageously, many processes described herein provide a methodology for meeting renewable fuel targets or mandates established by governments, including legislation and regulations for transportation or heating fuel sold or introduced into commerce in the United States. Examples of such legislation include the Energy Independence and Security Act ("EISA") and California AB 32—The Global Warming Solutions Act, which respectively established an RFS and a Low Carbon Fuel Standard (LCFS). For example, under EISA, the mandated annual targets of renewable content in fuel are implemented through an RFS that uses tradable credits (called Renewable Identification Numbers, referred to herein as "RINs") to track and manage the production, distribution and use of renewable fuels for transportation or other purposes. Targets under the LCFS can be met by trading of credits generated from the use of fuels with a lower GHG emission value than the gasoline baseline.

The term "credit", "renewable fuel credit" or "biofuel credit" means any rights, credits, revenues, greenhouse gas rights or similar rights related to carbon credits, rights to any greenhouse gas emission reductions, carbon-related credits or equivalent arising from emission reduction trading or any quantifiable benefits (including recognition, award or allocation of credits, allowances, permits or other tangible rights), whether created from or through a governmental authority, a private contract or otherwise. According to one embodiment of the invention, the renewable fuel credit is a certificate, record, serial number or guarantee, in any form, including electronic, which evidences production of a quantity of fuel meeting certain life cycle GHG emission reductions relative to a baseline set by a government authority. The baseline is typically a gasoline baseline. Non-limiting examples of credits include RINs and LCFS credits in the United States.

The fuel credit may be generated in connection with the biogenic carbon-based fuel that is used as a transportation or heating fuel. In one embodiment, a fuel credit is generated or caused to be generated with respect to the use of ethanol as a transportation or heating fuel.

The fuel credit can be generated or caused to be generated with respect to a biogenic carbon-based fuel that is the product produced from the biogenic carbon dioxide and fossil derived hydrogen, or a fuel derived therefrom.

The fuel credit can also be generated or caused to be generated with respect to a biogenic carbon-based fuel produced from the production process in which biogenic carbon dioxide is collected and used to produce the biogenic carbon-based fuel, fuel intermediate or chemical product. For example, a fuel credit can be generated with respect to methane sourced from biogas, which in turn is produced from anaerobic digestion of a stream from the production process in which the biogenic carbon dioxide is collected and used to make a product.

In one embodiment, the biogenic carbon-based fuel could qualify for an advanced biofuel RIN under EISA having a D code of 3, 4, 5 or 7. In a further embodiment, the product of the invention is eligible for a RIN having a D code of 3 or 5. Under the LCFS, products for use as fuels with greater reductions in life cycle GHG emissions qualify for a greater number of credits having higher market value than fuels with lower reductions.

Energy policy, including EISA and LCFS, and the generation of renewable fuel credits under each of these legislative frameworks, is discussed in turn below.

(a) Meeting Renewable Fuel Targets Under EISA

U.S. policymakers have introduced a combination of policies to support the production and consumption of biofuels, one of which includes the RFS. The RFS originated with the Energy Policy Act of 2005 (known as RFS1) and was expanded and extended by the EISA of 2007. The RFS expanded and extended under EISA is sometimes referred to as RFS2 or RFS as used herein.

Under the EISA, the RFS sets annual mandates for renewable fuels sold or introduced into commerce in the United States through 2022 for different categories of biofuels (see Table 2 below). There is an annually increasing schedule for minimum aggregate use of total renewable biofuel (comprised of conventional biofuels and advanced biofuels), total advanced biofuel (comprised of cellulosic biofuels, biomass-based diesel, and other advanced biofuels), cellulosic biofuel and bio-based diesel. The RFS mandates are prorated down to "obligated parties", including individual gasoline and diesel producers and/or importers, based on their annual production and/or imports.

Each year, obligated parties are required to meet their prorated share of the RFS mandates by accumulating credits known as RINs, either through blending designated quantities of different categories of biofuels, or by purchasing from others the RINs of the required biofuel categories.

The RIN system was created by the EPA to facilitate compliance with the RFS. Credits called RINs are used as a currency for credit trading and compliance. RINs are generated by producers and importers of renewable biofuels and assigned to the volumes of renewable fuels transferred into the fuel pool. RINs are transferred with a fuel through the distribution system until they are separated from the fuel by parties who are entitled to make such separation (generally refiners, importers, or parties that blend renewable fuels into finished fuels). After separation, RINs may be used for RFS compliance, held for future compliance, or traded. There is a centralized trading system administered by the U.S. EPA to manage the recording and transfer of all RINs.

According to certain embodiments of the invention, a RIN may be characterized as numerical information. The RIN numbering system was in the format KYYYYCCCCFFFFFBBBBBRRDSSSSSSSSEEEEEEEE where numbers are used to designate a code representing whether the RIN is separated from or attached to a specific volume (K), the calendar year of production or import (YYYY), Company ID (CCCC), Facility ID (FFFFF), Batch Number (BBBBB), a code for fuel equivalence value of the fuel (RR), a code for the renewable fuel category (D), the start of the RIN block (SSSSSSSS) and the end of the RIN block (EEEEEEEE). Under current regulations, a RIN contains much of the foregoing information and other information in the form of data elements that are introduced into a web-based system administered by the EPA known as the EPA Moderated Transaction System, or "EMTS". It should be appreciated, however, that the information required for RIN generation and/or the format of the information may change depending on prevailing regulations.

The D code of a RIN specifies the fuel type, feedstock and production process requirements and thus in certain embodiments of the invention the D code may be used to characterize the type of RIN, as described hereinafter. The D code of a RIN is assigned a value between 3 and 7 under current regulations. The value assigned depends on the fuel type, feedstock and production process requirements as described in Table 1 to 40 C.F.R. § 80.1426. Examples of fuels assigned a D code of 3-7 under current regulations are provided below. These examples are for illustration purposes only and are not to be considered limiting to the invention.

TABLE 1

RIN D code examples

| D code | Fuel Type | Example |
|---|---|---|
| 3 | Cellulosic biofuel | Ethanol from cellulosic biomass from agricultural residues |
| 4 | Biomass-based diesel | Biodiesel and renewable diesel from soy bean oil |
| 5 | Advanced biofuel | Ethanol from sugarcane |
| 6 | Renewable fuel (conventional biofuel) | Ethanol from corn starch |
| 7 | Cellulosic diesel | Diesel from cellulosic biomass from agricultural residues |

As described previously, the RFS2 mandate volumes are set by four separate but nested category groups, namely renewable biofuel, advanced biofuel, cellulosic biofuel and biomass-based diesel. The requirements for each of the nested category groups are provided in Table 2.

The nested category groups are differentiated by the D code of a RIN. To qualify as a total advanced biofuel, the D code assigned to the fuel is 3, 4, 5 or 7, while to qualify as cellulosic biofuel the D code assigned to the fuel is 3 or 7 (Table 2).

According to current regulations, each of the four nested category groups requires a performance threshold in terms of GHG reduction for the fuel type. In order to qualify as a renewable biofuel, a fuel is required to meet a 20% life cycle GHG emission reduction (or be exempt from this requirement), while advanced biofuel and biomass-based diesel are required to meet a 50% life cycle GHG emission reduction and cellulosic biofuels are required meet a 60% life cycle GHG emission reduction, relative to a gasoline baseline. As well, each nested category group is subject to meeting certain feedstock criteria.

TABLE 2

Nested category groups under RFS2

| Nested category group | Fuel type | Life cycle GHG threshold reduction relative to gasoline baseline |
|---|---|---|
| Renewable biofuel | Conventional biofuels (D code 6) and advanced biofuels (D code 3, 4, 5 or 7) | 20% |
| Advanced biofuel | Cellulosic biofuels (D code 3 or 7), biomass-based diesel (D code 4 or 7), and other advanced biofuels (D code 5) | 50% |
| Cellulosic biofuels | Biofuel derived from cellulosic material (D code 3) and bio-diesel derived cellulosic material (D code 7). | 60% |
| Biomass-based diesel | Conventional biodiesel (D code 4) or cellulosic diesel (D code 7) | 50% |

Thus, according one embodiment, a RIN credit containing information or a value corresponding to a reduction in life cycle GHG emissions relative to a baseline is generated with the production of a volume of biogenic carbon-based fuel produced by the process. The information may correspond to a reduction in life cycle GHG emissions of at least 40%, 45%, 50%, 55%, 60%, 65%, 70%, 75%, 80% or 85% relative to a gasoline baseline. In one embodiment, the processes described herein may contribute wholly or in part to achieving reductions in the life cycle GHG emissions of a biogenic carbon-based fuel relative to a gasoline baseline.

The RIN associated with biogenic carbon-based fuel may be assigned a D code of 3, 4, 5 or 7, also referred to herein as a D3, D4, D5 and D7 RIN, respectively. According to certain embodiments, the RIN associated with the biogenic carbon-based fuel may be assigned a D code of 3 or 5. Under current regulations, this corresponds to cellulosic biofuel and advanced biofuel fuel types, which meet GHG emissions reductions of 60% and 50%, respectively, relative to a gasoline baseline.

According to one embodiment, the fuel credit is characterized as containing numerical information associated with the one or more products produced by the process for use as a transportation or heating fuel. Thus, a party may generate a fuel credit comprising numerical information relating to one or more products of the process representing at least one parameter selected from (i) the type of transportation or heating fuel; (ii) the year in which the product was produced; (iii) a registration number associated with the producer or importer; and (iv) serial number associated with a batch. In one embodiment, at least two parameters or at least three parameters are selected from the foregoing list. The numerical information may also include one or more of the following parameters selected from: (i') a number identifying that the numerical information is assigned to a volume of the product, or separated; (ii') a registration number associated with the facility at which the product was produced or imported; (iii') a number representing a value related to an equivalence value of the product; (iv') a number representing a first-volume numerical information associated with a batch of the product; and (v') a number representing a last-volume numerical information associated with a batch of the product.

The RIN or numerical information described herein or a portion thereof is provided to a government regulatory agency, including the EPA, in connection with generating a RIN. In some embodiments of the invention, the numerical information is also provided to a purchaser of the biogenic carbon-based fuel produced by the invention. The numerical information described herein or portions thereof may be stored electronically in computer readable format.

The purchaser of the biogenic carbon-based fuel may separate the RIN. As described above, separation of a RIN from a volume of the biogenic carbon-based fuel for use as a transportation or heating fuel, means termination of the assignment of the RIN to a volume of fuel. RIN separation is typically carried out by a fuel blender, importer or other obligated party. According to pre-2010 regulations, when a RIN is separated, the K code of the RN is changed to 2.

Separation of RINs may be conducted in accordance with prevailing rules and regulations, as currently provided in 40 C.F.R. § 80.1129 and 40 C.F.R. § 80.1429. RINs generated in accordance with the processes described herein may be separated and subsequently traded.

It should be understood that the regulations under EISA, including RIN requirements and the criteria for categorization of a fuel under a particular fuel category, such as life cycle GHG emission thresholds, are described herein in accordance with current regulations and can be readily ascertained by those of skill in the art.

(b) Low Carbon Fuel Standard (LCFS)

The beneficial GHG emissions reductions achieved in some of these embodiments can provide a means for meeting low carbon fuel standards established by jurisdictions within the United States or other government authorities. The credit, which includes a certificate, may be associated with the biogenic carbon-based fuel, and represents or is proportional to the amount of life cycle GHG emissions reduced measured relative to a gasoline baseline. As set forth previously, the life cycle GHG emissions under low carbon fuel standards are often referred to as carbon intensity or CI.

California's LCFS currently requires that all mixes of fuel that oil refineries and distributors sell in the Californian market meet in aggregate the established targets for GHG emissions reductions. California's LCFS requires increasing annual reductions in the average life cycle emissions of most transportation fuels, up to a reduction of at least 10% in the carbon intensity, which is a measure of the life cycle GHG emissions, by 2020. Targets can be met by trading of credits generated from the use of fuels with a lower GHG emission value than gasoline baseline. Similar legislation has been implemented by the province of British Columbia, Canada, the United Kingdom and by the European Union.

According to one embodiments, LCFS fuel credit generation comprises generating information associated with the one or more products produced by the process of the invention for use as a transportation or heating fuel. A party may generate information relating to at least one parameter selected from (i) a reporting period; (ii) a fuel pathway code; (iii) transaction information, including type or date of a transaction; (iv) fuel production facility information; (v) fuel delivery methods; (vi) an amount of fuel used as a fossil fuel replacement, such as gasoline or diesel; and (vii) credits or deficits generated. In a further embodiment, information regarding at least two parameters, at least three parameters or at least four parameters is generated from the foregoing list.

British Columbia, a province in Canada, approved a Renewable and Low Carbon Fuel Requirements Act, which requires parties who manufacture or import the fuel into the province ensure that the renewable content and the average carbon intensity of the fuel they supply meets levels set by regulations. Fuel suppliers are required to submit annual reports regarding the renewable fuel content and carbon intensity of the transportation fuels they supply. The province allows transfers of GHG credits between fuel suppliers to provide flexibility in meeting the requirements of the regulation.

In the European Union, GHG emissions are regulated by a Fuel Quality Directive, 98/70/EC. In April 2009, Directive 2009/30/EC was adopted which revises the Fuel Quality Directive 98/70/EC. The revisions include a new element of legislation under Article 7a that requires fuel suppliers to reduce the GHG intensity of energy supplied for road transport (Low Carbon Fuel Standard). In particular, Article 7a specifies that this reduction should amount to at least 6% by 31 Dec. 2020, compared to the EU-average level of life cycle GHG emissions per unit of energy from fossil fuels in 2010. According to the Fuel Quality Directive, fuel/energy suppliers designated by member states of the European Union are required to report to designated authorities on: (a) the total volume of each type of fuel/energy supplied, indicating where the fuel/energy was purchased and its origin; and (b) the life cycle GHG emissions per unit of energy. The European Union has also promoted the use of biofuels through a Biofuel Directive (2003/30/EC), which mandates countries across the EU to displace certain percentages of transportation fuel with biofuels by target dates.

The United Kingdom has a Renewable Transport Fuel Obligation (RTFO) in which biofuel suppliers are required to report on the level of carbon savings and sustainability of the biofuels they supplied in order to receive Renewable Transport Fuel Certificates (RTFCs). Suppliers report on both the net GHG savings and the sustainability of the biofuels they supply according to the appropriate sustainability standards of the feedstocks from which they are produced and any potential indirect impacts of biofuel production, such as indirect land-use change or changes to food and other commodity prices that are beyond the control of individual suppliers. Suppliers that do not submit a report will not be eligible for RTFCs.

Certificates can be claimed when renewable fuels are supplied and fuel duty is paid on them. At the end of the obligation period, these certificates may be redeemed to the RTFO Administrator to demonstrate compliance. Certificates can be traded and if obligated suppliers do not have a sufficient amount of certificates at the end of an obligation period they may "buy-out" the balance of their obligation by paying a buy-out price.

Referring to FIG. 1, there is shown a process in accordance with one embodiment of the instant invention. In this embodiment, ethanol is produced as the result of two fermentations. In one of the fermentations, biogenic carbon dioxide and fossil derived hydrogen are fed to a bioreactor and fermented to ethanol by *Clostridium ljungdahlii* bacteria that carry out the following bioconversion:

$$6H_2 + 2CO_2 \rightarrow CH_3CH_2OH + 3H_2O.$$

The hydrogen is produced by a hydrogen production process using fossil methane as the feedstock. Fossil carbon dioxide produced from the hydrogen production that is otherwise vented is introduced underground to reduce life cycle GHG emissions of the final fuel/fuel intermediate. In the second fermentation, corn is fermented to produce ethanol.

Referring again to FIG. 1, corn is first treated by a dry milling process (not shown) that includes the steps of grinding the corn kernels, adding water to slurry the meal, and adding enzymes to convert the starch to glucose. The resultant slurry is then fed to carbohydrate fermentation unit 10 and fermented with *Saccharomyces cerevisiae* yeast to produce ethanol and a biogenic $CO_2$ stream 20, which has been purified in unit 15. In this embodiment, the $CO_2$ stream 20 contains about 100 mole % $CO_2$. The biogenic $CO_2$ stream 20 is combined with fossil derived hydrogen stream 30 to produce a combined stream 40 comprising biogenic $CO_2$ and fossil derived hydrogen.

A first step involved in producing the fossil derived hydrogen stream 30 involves feeding fossil methane stream 45 to a steam methane reformer (SMR) unit 50. The amount of methane in the fossil methane feed stream 45 to the SMR unit 50 is 92.9 mol %. In the steam methane reformer unit 50, the methane is converted to carbon monoxide and hydrogen by the following reaction with water to produce an SMR outlet stream 60 comprising carbon monoxide and hydrogen:

$$CH_4 + H_2O \rightarrow CO + 3H_2.$$

The SMR outlet stream 60 from the steam methane reformer unit 50 thus contains not only hydrogen from a fossil source, but also fossil carbon in the form of carbon monoxide. The fossil carbon monoxide in SMR outlet stream 60 is subsequently reacted with water to produce fossil carbon dioxide and additional hydrogen in a water gas shift (WGS) unit 70 as per the following reaction.

$$CO+H_2O \; CO_2+H_2.$$

The water gas shift unit 70 increases the yield of hydrogen from fossil methane, while converting the fossil CO to fossil carbon dioxide. In this embodiment, the water gas shift reaction in the water gas shift unit 70 comprises both a high and a low temperature shift (not shown). The overall conversion of fossil methane to carbon dioxide and hydrogen is as follows:

$$\text{Overall: } CH_4+2H_2O \rightarrow CO_2+4H_2.$$

An outlet stream 80 from the water gas shift unit 70 is then treated to remove carbon dioxide in carbon dioxide recovery unit 85 to produce a carbon dioxide-depleted stream 86 and a fossil carbon dioxide stream 87. The fossil carbon dioxide stream 87 is eventually introduced underground for enhanced oil recovery (EOR) 100. The carbon dioxide-depleted stream 86 is fed to a pressure swing adsorption (PSA) unit 90. The PSA unit 90 produces a stream enriched in fossil hydrogen, in this case at levels greater than 99 mol % hydrogen and a tail gas stream 91 comprising carbon dioxide, carbon monoxide, and hydrogen. The fossil carbon dioxide can be recovered from this purge stream 91 in another $CO_2$ recovery unit (not shown). Carbon dioxide can be recovered from other stages of the hydrogen production process as well, as for example from stream 220. In this embodiment, the purge stream 91 remaining after carbon dioxide removal is introduced to the furnace of the steam methane reformer unit 50 to provide heat energy to the unit.

The recovered fossil carbon dioxide is introduced to a pipeline (not shown) for transporting carbon dioxide. Carbon dioxide is withdrawn from the pipeline (not shown), typically by another party through a contractual arrangement, and then introduced underground to recover oil as part of an enhanced oil recovery operation (EOR) 100. By introducing the fossil carbon dioxide underground, the life cycle GHG emissions associated with biogenic ethanol produced by the process is significantly reduced.

The fossil derived hydrogen stream 30 comprising 99.9% mol % hydrogen is combined with the biogenic $CO_2$ stream 20 to form the combined stream 40, which is fed to the gas fermentation unit 110. In the gas fermentation unit 110, the biogenic carbon dioxide and fossil derived hydrogen are fermented to ethanol by *Clostridium ljungdahlii* bacteria.

A fermented stream 120 is withdrawn from the gas fermentation unit 110 and subject to a solid liquid separation that provides a relatively concentrated stream of cells 112 and a stream of ethanol 114 (i.e., wherein the cells have been substantially depleted). The ethanol stream 114 is fed to carbohydrate fermentation unit 10, either directly or at some stage of the process upstream of the carbohydrate fermentation unit 10. The *Saccharomyces cerevisiae* yeast in fermentation unit 10 produce ethanol stream 12 and biogenic $CO_2$ stream 20 from the feedstock added to the fermentation 10. Ethanol stream 12, which includes ethanol produced in the gas 110 and carbohydrate 10 fermentations, is fed to a recovery unit 13 that produces concentrated biogenic ethanol and still bottoms. The concentrated biogenic ethanol may be further concentrated beyond its azeotropic breaking point by molecular sieves (not shown). The still bottoms are fed to an evaporator 16 that produces a concentrated still bottoms stream 17 and a condensate stream 18, the latter of which is recycled back into the gas fermentation unit 110.

Advantageously, providing the ethanol stream produced from the gas fermentation 110 to the carbohydrate fermentation unit 10 (e.g., directly or indirectly), increases the concentration of ethanol in effluent stream 12 and/or maintains the concentration of ethanol in effluent stream 12 with utilization of less corn. In addition to increasing the total ethanol yield for a given amount of substrate, providing the two fermentations has various synergetic advantages. For example, as discussed above, providing a more concentrated combined ethanol stream to the distillation 13 further reduces the relative overall ethanol recovery costs in comparison with separate product recovery processes on each fermentation stream. For example, as discussed above, providing a single distillation system to recover the gas and carbohydrate fermentation products reduces capital and operating costs related to a simpler system and the processing of less total water. In addition, distilling an effluent having a higher concentration of fermentation product produces more fermentation product for about the same operating costs (e.g., related to energy for distilling a same volume of effluent). Notably, simply combining the two effluents in a single distillation system provides a fermentation product concentration that is lower than the concentration of fermentation product in the carbohydrate fermentation unit effluent and would thus involve more water processing per unit of ethanol. Furthermore, since the gas fermentation product does not have to be recovered in a separate step, a fuel or fuel intermediate containing the gas fermentation product should still have a life-cycle GHG emission that meets the requirements for various fuel credits.

Figure 2:
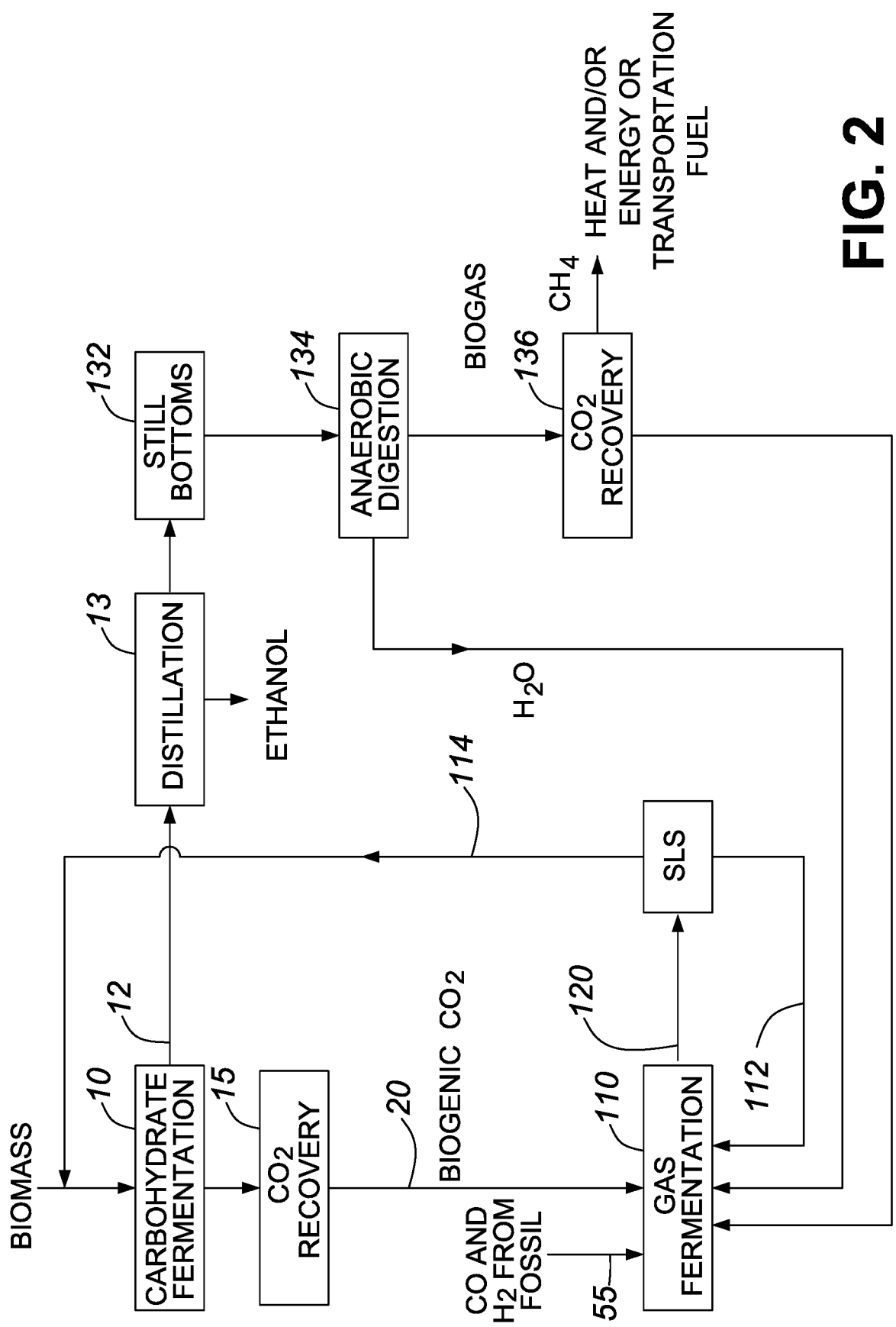
FIG. 2 is a process flow diagram showing the production of biogenic ethanol in accordance with one embodiment of the invention.

Referring to FIG. 2, there is shown a process in accordance with another embodiment of the instant invention. In this embodiment, ethanol is produced as the result of two fermentations. In one of the fermentations, biogenic carbon dioxide, fossil derived carbon monoxide, and fossil derived hydrogen are fed to a bioreactor containing *Clostridium ljungdahlii* and fermented to ethanol. More specifically, with reference to FIG. 2, the biogenic $CO_2$ stream 20 is combined with a fossil syngas stream 55. The syngas stream 55 results from the conversion of fossil methane to fossil carbon monoxide and fossil hydrogen by a steam methane reforming unit in which the following reaction is carried out:

$$CH_4+H_2O \rightarrow CO+3H_2.$$

Since no water gas shift reaction occurs and no $CO_2$ is introduced underground, the syngas stream 55 blended with stream 20 contains not only hydrogen from a fossil source, but also fossil carbon in the form of carbon monoxide. The fossil syngas stream 55 contains about 49.1 mol % fossil hydrogen and 9.7 mol % carbon monoxide (wet basis).

Referring to FIG. 2, the biogenic carbon dioxide 20 and the fossil syngas 55 (e.g., comprising carbon monoxide, carbon dioxide and hydrogen from fossil fuel) are combined in the fermentation bioreactor 110 and are fermented to ethanol by *Clostridium ljungdahlii* bacteria contained therein. The following reactions occur to produce ethanol:

$$6CO+3H_2O \rightarrow CH_3CH_2OH+4CO_2$$

$$6H_2+2CO_2 \rightarrow CH_3CH_2OH+3H_2O.$$

A fermented stream 120 is withdrawn from the fermentation bioreactor 110 and subject to a solid liquid separation that provides a first stream containing the cells 112 and a second stream containing ethanol 114 (i.e., an effluent stream wherein the cells have been substantially depleted). The ethanol stream 114 is fed to the second fermentation.

In the second fermentation, biomass that has been processed in one or more processing steps (e.g., pretreatment and/or hydrolysis) to provide a carbohydrate is fed to the carbohydrate fermentation unit 10, which contains *Saccharomyces cerevisiae*.

The effluent from the gas fermentation reactor 110, which includes relatively dilute ethanol, is filtered and introduced with the biomass to the carbohydrate fermentation unit 10. The aqueous stream comprising alcohol 114 is added prior to or during a step of the pretreatment/hydrolysis/fermentation that requires water. For example, the biomass may be added to the aqueous stream to form the slurry and/or the aqueous stream prior to thelocation where the enzymes are added. The carbohydrate fermentation unit 10, to which *Saccharomyces cerevisiae* yeast has been introduced, produces ethanol 12 and a biogenic $CO_2$ stream 20, which is purified in unit 15. Ethanol stream 12, which includes ethanol produced in the gas fermentation unit 110 and carbohydrate fermentation unit 10, is fed to a distillation unit 13 to produce concentrated ethanol and still bottoms. The concentrated ethanol is further concentrated beyond its azeotropic breaking point by molecular sieves (not shown).

Advantageously, providing the ethanol stream produced from the gas fermentation 110 to the carbohydrate fermentation unit 10, allows the relatively dilute ethanol stream 114 to be combined with the ethanol provided as a result of the carbohydrate fermentation to increase the concentration of the ethanol after distillation 13 or to produce the same concentration of ethanol with utilization of less biomass. In addition to increasing the total ethanol yield per unit of biomass, providing two fermentations has various synergetic advantages. For example, as discussed above, providing a combined ethanol stream to the distillation unit 13 reduces the relative ethanol recovery costs (e.g., per unit of ethanol) in comparison to separate distillation systems.

Further advantageously, the still bottoms 132 from the distillation are subject to an anaerobic digestion 134 that produces biogas. The $CO_2$ in the biogas is fed to the gas fermentation reactor 110 to increase the production of ethanol in the gas fermentation unit, while the methane in the biogas is used for heat and/or energy within the process (e.g., distillation) or as a transportation fuel or fuel intermediate. Water is recycled from the anaerobic digestion 134 to the gas fermentation unit (e.g., backset).

Figure 3:
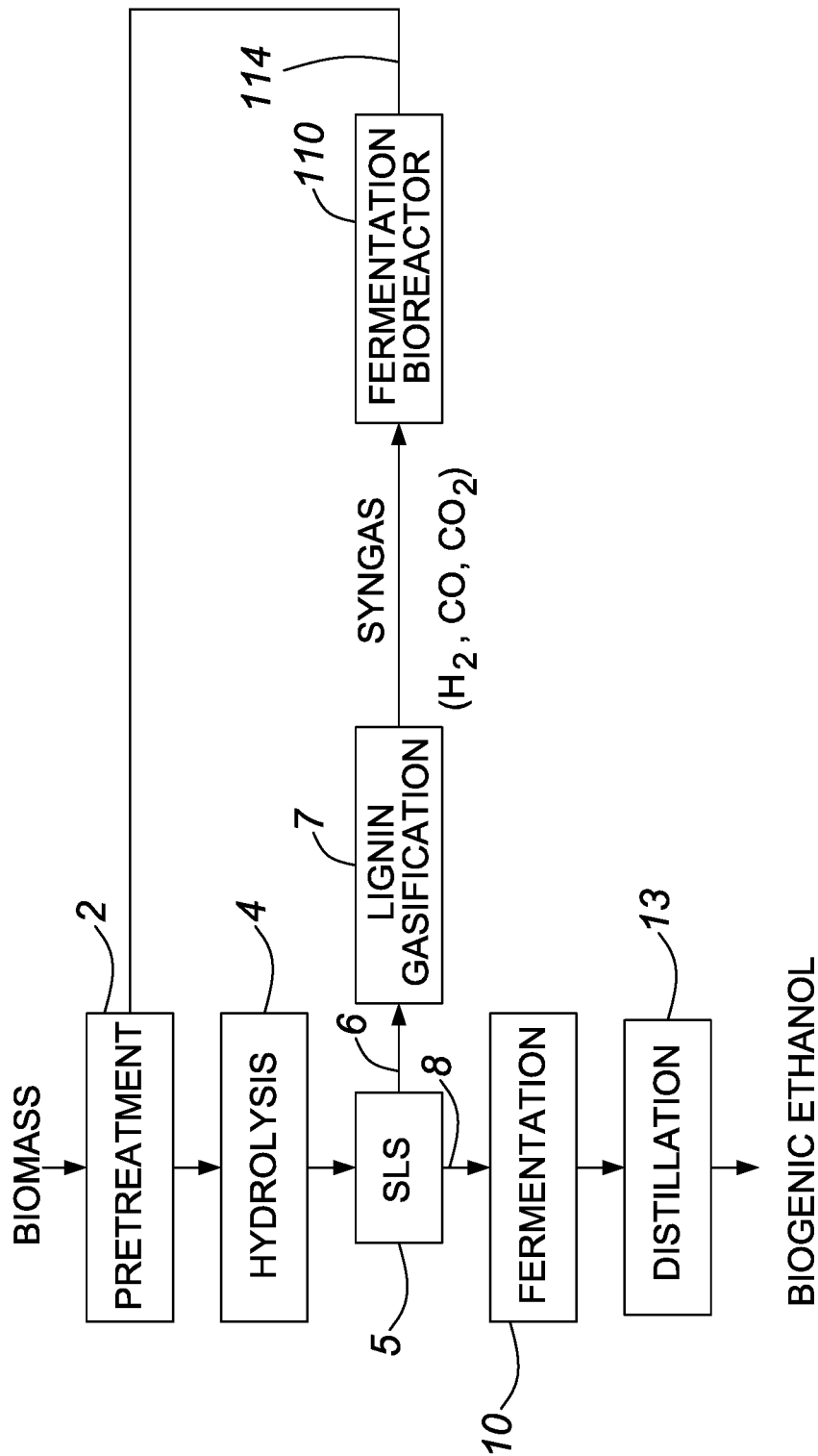
FIG. 3 is a process flow diagram showing the production of biogenic ethanol in accordance with one embodiment of the invention.

Referring to FIG. 3, there is shown a process in accordance with another embodiment of the instant invention. In this embodiment, ethanol is produced as the result of two fermentations. In one of the fermentations, syngas produced from the gasification of lignin is fed to a bioreactor and fermented to ethanol.

Referring to FIG. 3, the syngas (e.g., including carbon monoxide, carbon dioxide and/or hydrogen) is introduced to the fermentation bioreactor 110 and is fermented to ethanol by *Clostridium ljungdahlii* bacteria. The following reactions occur to produce ethanol:

$$6CO+3H_2O \rightarrow CH_3CH_2OH+4CO_2$$

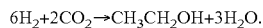

$$6H_2+2CO_2 \rightarrow CH_3CH_2OH+3H_2O.$$

A fermented stream is withdrawn from the fermentation bioreactor 110 and subject to a solid liquid separation (not shown) that removes the cells to provide an aqueous stream containing ethanol 114. The relatively dilute ethanol stream 114 is fed the second fermentation. Optionally, a stream of fossil hydrogen is added to the bioreactor 110.

In the second fermentation, biomass (e.g., a cellulosic feedstock) is subjected to a pretreatment 2 (e.g., an acid pretreatment, an alkali pretreatment, or hydrothermal pretreatment). At least some of the water required for the pretreatment 2 and/or hydrolysis 4 is sourced from the aqueous stream 114 containing ethanol. The hydrolysate is subject to a solid/liquid separation 5 that provides lignin 6 and a stream comprising a sugar 8 (e.g., glucose). The stream comprising sugar is fed to the fermentation unit 10, to which *Saccharomyces cerevisiae* yeast has been introduced, to produce ethanol. The lignin is subject to gasification 7 to provide syngas, which serves as the substrate for the gas fermentation. The effluent from the fermentation reactor 10, which includes the ethanol produced by the gas fermentation and the ethanol produced by the carbohydrate fermentation, is fed to a recovery 13 to produce concentrated biogenic ethanol. The concentrated biogenic ethanol may be further concentrated beyond its azeotropic breaking point by molecular sieves (not shown).

Advantageously, providing the ethanol stream produced from the gas fermentation 110 to the carbohydrate fermentation unit 10 allows the relatively dilute ethanol stream 114 provided by the gas fermentation 110 to be combined with the ethanol provided as a result of the carbohydrate fermentation to provide an ethanol stream that has a concentration that is at least 25 g/L higher than the ethanol stream 114 provided from gas fermentation 110. In addition to increasing the total ethanol yield, providing two fermentations has various synergetic advantages. For example, as discussed above, providing a more concentrated ethanol stream to recovery reduces the relative ethanol recovery costs (e.g., per unit of ethanol) in comparison with separate distillations, and thus may contribute favorably to green house gas emission reductions.

In this embodiment, the fermentation product from each of the gas and carbohydrate fermentation reactors is ethanol. Alternatively, the fermentation condition may be adjusted such the fermentation product from each of the gas and carbohydrate fermentations is a different fuel or fuel intermediate. In one embodiment, the fermentation product from the gas fermentation is converted to ethanol prior to being introduced to or upstream of the carbohydrate fermentation.

Figure 4:
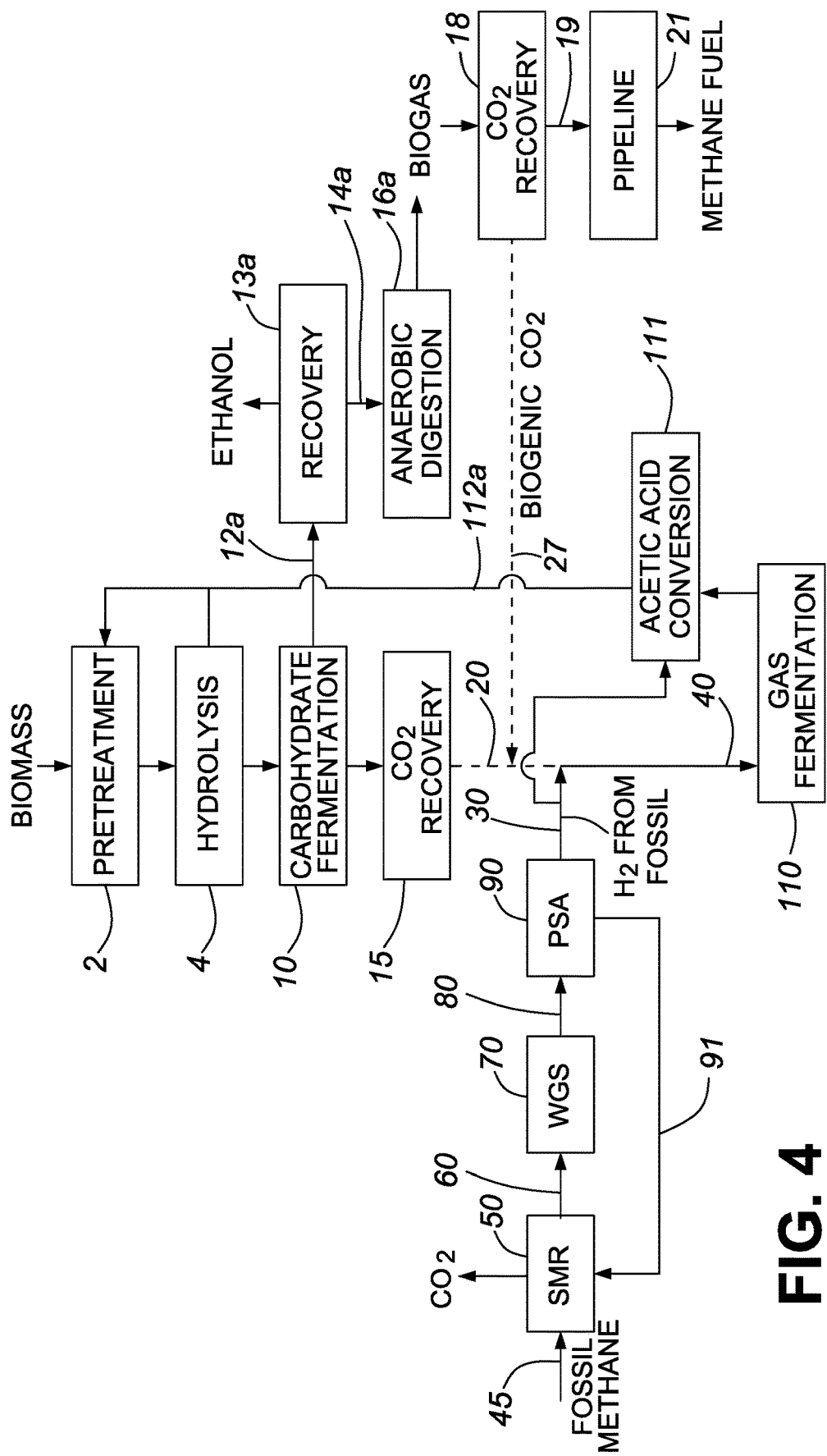
FIG. 4 is a process flow diagram showing the production of biogenic ethanol in accordance with one embodiment of the invention.

Referring to FIG. 4, there is shown a process in accordance with another embodiment of the instant invention. In this embodiment, biogenic carbon dioxide and/or carbon monoxide and fossil derived hydrogen are fed to a gas fermentation unit and fermented to acetic acid using suitable bacteria. In this embodiment, the bacteria is *Clostridium ljungdahlii*. In one embodiment the bacteria include anaerobes that use the Wood-Ljungdahl pathway. These acetogens use $CO_2$ and $H_2$, and/or CO to produce acetic acid according to the following stoichiometries:

$$2CO_2+4H_2 \rightarrow CH_3COOH+2H_2O$$

$$4CO+2H_2O \rightarrow CH_3COOH+2CO_2.$$

The hydrogen is produced by a hydrogen production process using fossil methane as the feedstock. Fossil carbon dioxide produced from the hydrogen production that is otherwise vented may be introduced underground to reduce life cycle GHG emissions of the final fuel/fuel intermediate.

In the other fermentation, which is a carbohydrate fermentation, carbohydrate produced from biomass in one or more processing steps, is converted to ethanol using a suitable yeast (e.g., *Saccharomyces cerevisiae*) under conditions suitable for such yeast and product as known in the art.

Referring to FIG. 4, biomass, which corresponds to a lignocellulosic feedstock, is fed to pretreatment 2 (e.g., dry or as a slurry). The pretreatment 2, which involves the addition of heat and may also involve the addition of acid or base, helps to liberate the cellulose from the lignin and/or makes the biomass more amenable to the hydrolysis 4. In hydrolysis 4, which is enzymatic, the cellulose is converted to a sugar (e.g., glucose). In fermentation 10, the sugar is converted to ethanol using *Saccharomyces cerevisiae* yeast. The ethanol is recovered 13*a* from the effluent stream 12*a* to provide relatively pure ethanol and to provide an effluent 14*a* that is fed to anaerobic digestion 16*a*, which produces biogas.

In the gas fermentation unit 110, feedstock including at least $CO_2$ and $H_2$ is converted to acetic acid by *Clostridium ljungdahlii* bacteria. The effluent from the gas fermentation 110 is then subject to a solid liquid separation (not shown) that recycles the cells back to the fermentation unit 110 and provides a stream containing acetic acid.

The acetic acid is then converted 111 to ethanol. In a first step, the acetic acid is recovered (e.g., concentrated and/or purified using methods known in the art such as extraction followed by distillation, or salt formation and evaporation). The purified acetic acid is then subject to a hydrogenation using hydrogen gas to provide ethanol in unit 111, which is provided as an aqueous stream 112*a* to or upstream of the carbohydrate fermentation.

Referring again to FIG. 4, $H_2$ for the gas fermentation feedstock and for the acetic acid conversion is provided by steam reforming of fossil methane. In particular, the fossil derived hydrogen stream 30 is prepared by feeding fossil methane stream 45 to a steam methane reformer (SMR) unit 50. In the steam methane reformer unit 50, the methane is converted to carbon monoxide and hydrogen when reacted with water. The SMR outlet stream 60 from the steam methane reformer unit 50 thus contains not only hydrogen from a fossil source, but also fossil carbon in the form of carbon monoxide. The fossil carbon monoxide in SMR outlet stream 60 is subsequently reacted with water to produce fossil carbon dioxide and additional hydrogen in a water gas shift (WGS) unit 70. The water gas shift unit 70 increases the yield of hydrogen from fossil methane, while converting the fossil CO to fossil carbon dioxide. An outlet stream 80 from the water gas shift unit 70 is fed to a pressure swing adsorption (PSA) unit 90. The PSA unit 90 produces a stream enriched in fossil hydrogen, in this case at levels greater than 99 mol % hydrogen and a tail gas stream 91 comprising carbon dioxide, carbon monoxide, and hydrogen. The fossil carbon dioxide is recovered from this purge stream 91 in another $CO_2$ recovery unit (not shown). In this embodiment, the purge stream 91 remaining after carbon dioxide removal is introduced to the furnace of the steam methane reformer unit 50 to provide heat energy to the unit. The recovered $CO_2$, or an equivalent amount of recovered fossil derived $CO_2$, is introduced underground (not shown) in order to reduce life-cycle GHG emissions of ethanol produced from overall process.

In this embodiment, the acetic acid is an intermediate in the production of ethanol, which is the desired fermentation product. Accordingly, although the gas fermentor 110 produces acetic acid, the ethanol derived from the acetic acid may be considered to be the fermentation product. More specifically, the gas substrate is provided to the gas fermentor to produce ethanol (e.g., indirectly via the production of acetic acid).

In this embodiment, biogenic $CO_2$ is collected from various steps of the process (e.g., at 15, 18) and used as feedstock for the gas fermentation. For example, the biogenic $CO_2$ collected from the biogas generated during the anaerobic digestion 16*a* is recovered 19, while the remaining biogas stream 29 is purified and introduced to a pipeline 21.

In one embodiment, the ethanol stream 112*a* is introduced into the process at one or more steps of the process that require the addition of water and/or dilution. For example, the ethanol stream is introduced directly to the biomass, at the pretreatment stage 2, at the hydrolysis stage 4, and/or at the fermentation stage 10. Since these stages require additional water, the addition of the ethanol stream 112*a* provides water recycle/reduction (i.e., reduces the amount of clean water imported and/or treated water recycled) and also stacks the product (e.g., adds product to product), thus increasing the concentration of the product(s).

In each of the above described examples, at least part of the aqueous stream containing the gas fermentation product is introduced to and/or used in another stage of the process (e.g., where there is a high percentage of solids). As described above, one advantage to recycling the gas fermentation product stream is that it may reduce the amount of water required to be sourced externally from the process, while also increasing the yield of biogenic fuel and/or fuel intermediate for a given amount of feedstock. In addition, it reduces the amount of energy required to recover the fermentation product provided in the aqueous stream 112*a*, thus also providing cost savings and life cycle GHG savings.

Another advantage to recycling the aqueous gas fermentation product stream is that it exploits some of the benefits of gas fermentation while minimizing the disadvantages of gas fermentation. For example, gas fermentation of $CO_2$ and $H_2$ and/or CO in the presence of suitable microbes provides a method of obtaining valuable biofuels from gaseous waste streams using microbial processes that may operate at ambient temperatures and low pressures, thus offering energy and cost savings. However, the microorganisms for syngas fermentation are also often associated with low production rates, low broth concentrations, and/or a low product tolerance. With respect to the latter, acetogens used in gas fermentation often exhibit low resistance towards products such as ethanol and butanol. In general, the product concentration in the gas fermentation broth may be reduced by providing in situ product recovery and/or by adding water to the gas fermentation unit to dilute the product, and hence reduce toxicity. In conventional gas fermentations, there is often a fine balance between adding sufficient water to reduce product inhibition and reducing the amount of water added to minimize product recovery costs. In contrast, by providing a process in which an aqueous stream comprising the gas fermentation product or a derivative thereof is introduced into the process at or upstream of the carbohydrate fermentation, the amount of water added to the gas fermentation unit to reduce product inhibition will not be limited by recovery costs of the fermentation product.

Further advantageously, the microorganisms typically used in the carbohydrate fermentation, such as yeasts, have a higher tolerance to fermentation products (e.g., such as ethanol) than the microorganisms used in gas fermentation. Accordingly, feeding the gas fermentation effluent stream (e.g., cell depleted) or a derivative thereof to the carbohydrate fermentation or a step upstream of the carbohydrate fermentation may even kill bacteria in the carbohydrate fermentation, thus functioning as a biocide to kill unwanted bacteria therein (e.g., product inhibition is not as limiting for the microorganisms used in the carbohydrate fermentation as it is for those in the gas fermentation).

As described above, introducing the cell-depleted effluent stream from the gas fermentation into the carbohydrate fermentation and/or upstream of the carbohydrate fermentation may introduce not only the desired end product, but also any byproducts and/or impurities, to the carbohydrate fermentation. However, since gas fermentations are often very product selective and efficient, and since the carbohydrate fermentation is relatively unaffected by the products and/or byproducts of the gas fermentation, the conventional step of recovering the product directly from the gas fermentation may be eliminated, thus simplifying the overall process.

Another advantage of combining gas fermentation with carbohydrate fermentation is that the vent (e.g., exhaust) gas from the gas fermentation may be used as an energy source to process the feedstock fed to the carbohydrate fermentation, as an energy source for product recovery (e.g., distilling ethanol), as an energy source to generate additional hydrogen, as a feedstock to make additional hydrogen, as a source of $CO_2$ for use in EOR, and/or to produce a recycle stream via one or more processing steps that is introduced to the carbohydrate fermentation.

As described above, the gas fermentation allows acetogens such as *C. ljungdahlii, C. carboxidivorans, C. ragsdalei*, and *C. autoethanogenum*, to metabolize CO, and/or $CO_2/H_2$ found in existing feedstocks (e.g., gas streams inherently generated in a biofuel production plant, e.g., corn, cellulosic, etc.) to provide valuable products such as ethanol, butanol, isopropanol, 2,3-butanediol, acetic acid and/or butyric acid that can be introduced into stages of the biofuel production process to increase yield of biofuel from a given feedstock and/or decrease recovery costs per unit of product. However, as also described above, the feedstock for the gas fermentation may be provided only by CO-rich off-gas streams generated in industries such as natural gas steam reforming, oil refining, steel mill, and/or chemical production, regardless of whether the carbon monoxide therein is fossil carbon monoxide. In embodiments wherein the feedstock is provided by natural gas steam reforming, the steam reformer may be provided within the biofuel production plant. In other embodiments, the off-gas streams produced by the selected industry may be exported to a biofuel production plant, or the feedstock for the carbohydrate fermentation may be imported to the selected industry from a third party. In the latter case, the feedstock may be added to the cell-depleted effluent of the gas fermentation in another fermentation unit. In each case, integrating the two sequential fermentations may reduce capital and operating costs (e.g., related to reduced recovery costs and/or less feedstock) in comparison with independent product recovery. Moreover, providing an aqueous stream containing fermentation product from the first fermentation to the second bioreactor and/or a stage upstream of the second bioreactor, to a stream or process that otherwise would require the addition of clean and/or treated water, improves product yield for a given energy input or feedstock amount, while providing water recycle.

Of course, the above embodiments have been provided as examples only. It will be appreciated by those of ordinary skill in the art that various modifications, alternate configurations, and/or equivalents will be employed without departing from the spirit and scope of the invention. For example, although the gas fermentations and/or the carbohydrate fermentations described in the examples only use one microorganism (e.g., in a predetermined amount), in other embodiments, two or more microorganisms are provided. Furthermore, although the gas fermentation and carbohydrate may be referred to as a first fermentation and a second fermentation herein, there is no order implied. For example, in one embodiment, the carbohydrate fermentation is run first and then the gas fermentation product is added at some point during carbohydrate fermentation (e.g., the carbohydrate and/or gas fermentations may be run continuously). Accordingly, the scope of the invention is therefore intended to be limited solely by the scope of the appended claims.

The invention claimed is:

1. A process for producing ethanol comprising:
   (i) obtaining methane sourced from biogas, said biogas produced from anaerobic digestion;
   (ii) reforming a gas to produce syngas, said gas comprising the methane sourced from biogas;
   (iii) converting one or more components of the syngas to ethanol, said converting comprising subjecting a gas substrate comprising the one or more components to a gas fermentation, said one or more components comprising carbon monoxide, carbon dioxide, hydrogen, or a combination thereof;
   (iv) using an aqueous stream comprising ethanol produced in (iii) in an ethanol production process that comprises fermenting carbohydrate to ethanol,
   wherein step (iv) comprises feeding said aqueous stream to a stage in the ethanol production process such that ethanol produced in (iii) is copresent with carbohydrate during at least part of a step of fermenting said carbohydrate to ethanol.

2. The process according to claim 1, comprising recovering ethanol produced in (iii) together with ethanol produced by fermenting said carbohydrate to ethanol.

3. The process according to claim 2, wherein said gas substrate comprises carbon dioxide produced from fermenting said carbohydrate to ethanol.

4. The process according to claim 2, wherein said ethanol production process is a cellulosic ethanol production process, and wherein said biogas comprises biogas produced from anaerobic digestion of still bottoms produced in said cellulosic ethanol production process.

5. The process according to claim 4, wherein said gas reformed in step (ii) comprises fossil methane.

6. The process according to claim 4, comprising:
   (a) converting fossil methane to carbon monoxide and hydrogen by reforming;
   (b) converting at least a portion of the carbon monoxide produced in (a) by a water-gas shift reaction to carbon dioxide, thereby producing a stream comprising carbon dioxide and hydrogen; and
   (c) separating at least a portion of the hydrogen from the stream of step (b) from non-hydrogen components to produce a stream enriched in hydrogen and a stream comprising carbon dioxide;
   wherein said gas substrate comprises hydrogen from the stream enriched in hydrogen.

7. The process according to claim 6, wherein said gas substrate comprises carbon dioxide produced from carbohydrate fermentation in said cellulosic ethanol production process.

8. The process according to claim 7, wherein said gas substrate comprises hydrogen and carbon dioxide in amounts sufficient to provide a molar ratio of hydrogen to carbon dioxide between 2:1 and 4:1.

9. A process for producing ethanol comprising:
   (i) treating a feedstock to obtain a fermentable carbohydrate;
   (ii) fermenting said fermentable carbohydrate to produce ethanol;
   (iii) feeding a portion of the treated feedstock not converted to ethanol to an anaerobic digester;

(iv) collecting biogas from said anaerobic digester;
(v) converting one or more components of said collected biogas to ethanol, said converting comprising fermenting a gas substrate comprising one or more components obtained or derived from the collected biogas, said one or more components selected from carbon monoxide, carbon dioxide, and hydrogen; and
(vii) using an aqueous stream comprising ethanol produced in step (v) within the process such that ethanol produced in step (v) is copresent with fermentable carbohydrate for at least part of a step of fermenting said fermentable carbohydrate to produce ethanol.

10. The process according to claim 9, wherein converting one or more components of said collected biogas to ethanol comprises:
reforming a gas to produce syngas, wherein said gas comprises methane from said collected biogas, and wherein said gas substrate comprises one or more components of the syngas.

11. The process according to claim 9, wherein converting one or more components of said collected biogas to ethanol comprises:
subjecting a gas to a steam reforming process to produce syngas, wherein said gas comprises said collected biogas and carbon dioxide produced from fermenting said fermentable carbohydrate, wherein said gas substrate comprises one or more components of the syngas.

12. The process according to claim 9, comprising collecting carbon dioxide produced from fermenting said fermentable carbohydrate, wherein said gas substrate comprises said collected carbon dioxide.

13. The process according to claim 12, comprising:
(a) converting fossil methane to carbon monoxide and hydrogen by reforming;
(b) converting at least a portion of said carbon monoxide by a water-gas shift reaction to carbon dioxide, thereby producing a stream comprising carbon dioxide and hydrogen; and
(c) separating at least a portion of the hydrogen from the stream of step (b) from non-hydrogen components to produce a stream enriched in hydrogen and a stream comprising carbon dioxide;
wherein said gas substrate comprises hydrogen from said stream enriched in hydrogen.

14. The process according to claim 9, comprising:
(a) converting fossil methane to carbon monoxide and hydrogen by reforming;
(b) converting at least a portion of said carbon monoxide by a water-gas shift reaction to carbon dioxide, thereby producing a stream comprising carbon dioxide and hydrogen; and
(c) separating at least a portion of said hydrogen from the stream of step (b) from non-hydrogen components to produce a stream enriched in hydrogen and a stream comprising carbon dioxide;
wherein said gas substrate comprises hydrogen from the stream enriched in hydrogen.

15. The process according to claim 9, comprising recovering ethanol produced in step (v) and ethanol derived from the fermentable carbohydrate.

16. The process according to claim 9, wherein said portion of treated feedstock not converted to ethanol and fed to anaerobic digestion comprises still bottoms.

17. The process according to claim 9, wherein said gas substrate comprises hydrogen and carbon dioxide in amounts sufficient to provide a molar ratio of hydrogen to carbon dioxide between 2:1 and 4:1.

18. The process according to claim 9, wherein said gas substrate is syngas produced by reforming said collected biogas.

19. The process according to claim 9, wherein said gas substrate comprises syngas produced by reforming said collected biogas, hydrogen derived from fossil methane, carbon dioxide collected from carbohydrate fermentation, or any combination thereof.

* * * * *

UNITED STATES PATENT AND TRADEMARK OFFICE
CERTIFICATE OF CORRECTION

PATENT NO. : 10,894,969 B2
APPLICATION NO. : 16/244767
DATED : January 19, 2021
INVENTOR(S) : Patrick J. Foody It is certified that error appears in the above-identified patent and that said Letters Patent is hereby corrected as shown below:

On the Title Page

On page 3, in Column 2, item (56), Other Publications, Line 15, delete "www/global" and insert --www.global--.

On page 3, in Column 2, item (56), Other Publications, Line 15, delete "/ project/" and insert --/project/--.

On page 3, in Column 2, item (56), Other Publications, Line 32, delete "Natural Fas" and insert --Natural Gas--.

On page 3, in Column 2, item (56), Other Publications, Line 35, delete "NREL/ TP" and insert --NREL/TP--.

On page 4, in Column 1, item (56), Other Publications, Line 22, delete "Oili" and insert --Oil--.

On page 4, in Column 1, item (56), Other Publications, Line 28, delete "ZnO/Al2O3" and insert --ZnO/Al$_2$O$_3$--.

On page 5, in Column 1, item (56), Other Publications, Line 11, delete "( 2000)," and insert --(2000),--.

In the Specification

In Column 3, Line 6, delete "etc)" and insert --etc.)--.

In Column 19, Line 25, delete "a can" and insert --can--.

In Column 24, Line 7, delete "N-methyl 2 pyrrolidone," and insert --N-methyl-2-pyrrolidone,--.

Signed and Sealed this
Twenty-seventh Day of April, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,894,969 B2

In Column 28, Line 51, delete "CO2" and insert --$CO_2$--.

In Column 32, Line 58, delete "RN" and insert --RIN--.

In Column 33, Line 26, delete "embodiments," and insert --embodiment,--.

In Column 35, Line 5, delete "CO+H2O CO2+H2." and insert --$CO+H_2O \rightarrow CO_2+H_2$.--.

In Column 37, Line 13, delete "thelocation" and insert --the location--.

In Column 38, Line 31, delete "green house" and insert --greenhouse--.

In the Claims

In Column 42, Line 44, Claim 6, delete "water-gas" and insert --water gas--.

In Column 43, Line 8, Claim 9, delete "(vii)" and insert --(vi)--.

In Column 43, Line 37, Claim 13, delete "water-gas" and insert --water gas--.

In Column 44, Line 11, Claim 14, delete "water-gas" and insert --water gas--.